(12) United States Patent
Smith et al.

(10) Patent No.: US 11,167,048 B2
(45) Date of Patent: Nov. 9, 2021

(54) DUAL TARGETING LIGAND FOR CANCER DIAGNOSIS AND TREATMENT

(71) Applicant: The Curators of the University of Missouri, Columbia, MO (US)

(72) Inventors: Charles Jeffrey Smith, Columbia, MO (US); Rajendra Prasad Bandari, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 16/713,468

(22) Filed: Dec. 13, 2019

(65) Prior Publication Data

US 2020/0188539 A1    Jun. 18, 2020

Related U.S. Application Data

(60) Provisional application No. 62/779,623, filed on Dec. 14, 2018.

(51) Int. Cl.
*A61P 35/00* (2006.01)
*A61K 51/08* (2006.01)
*A61K 51/04* (2006.01)

(52) U.S. Cl.
CPC .......... *A61K 51/0482* (2013.01); *A61K 51/08* (2013.01); *A61P 35/00* (2018.01)

(58) Field of Classification Search
CPC ............ A61K 2121/00; A61K 2123/00; A61K 51/00; A61K 51/08; A61K 51/088; A61K 51/0497; A61K 51/0402; A61K 51/04; A61K 51/0482
USPC ........ 424/1.11, 1.65, 1.69, 9.1, 9.2, 9.3, 9.4, 424/9.5, 9.6; 534/7, 10–16; 514/1, 1.1, 514/19.2, 19.3, 19.4, 19.5, 19.6; 530/300
See application file for complete search history.

(56) References Cited

U.S. PATENT DOCUMENTS

2020/0031623 A1* 10/2020 Garrison et al. ... A61K 51/0497
424/1.65

OTHER PUBLICATIONS

Afshar-Oromieh et al., I[68Ga]Gallium-labelled PSMA ligand as superior PET tracer for the diagnosis of prostate concer: comparison with 18F-FECH; Eur. J. Nucl. Med. Mol. Imaging, 2012; vol. 39, pp. 1085-1086.
Bandari et al., Syntheiss and Biological Evaluation of Copper-64 Radiolabeled [DUPA-6-Ahx-(NODAGA)-5-Ava-BBN(7-14)NH2], a Novel Bivalent Targeting Vector Having Affinity for Two Distinct Biomarkers (GRPr/PSMA) of Prostate Cancer.
Beheshti et al., BAY 1075553 PET-CT for Staging and Restaging Prostate Cancer Patients: Comparison with [18F] Fluorocholine PET-CT (Phase I Study); Mol. Imaging Biol., 2015, vol. 17, pp. 424-433.
Breeman et al., Preclinical Comparison of 111In-Labeled DTPA-or DOTA-Bombesin Analogs for Receptor-Targeted Scintigraphy and Radionuclide Therapy; JNM SNM Journals; Feb. 20, 2020; 8-pages.
Chen et al., microPET and Autoradiographic Imaging of GRP Receptor Expression with 64Cu-DOTA-[Lys3]Bombesin in Human Prostate Adenocarcinoma Xenografts; JNM SNM Journals; Feb. 20, 2020, 9-pages.
Cho et al., Biodistribution, Tumor Detection, and Radiation Dosimetry of 18F-DCFBC, a Low-Molecular-Weight Inhibitor of Prostate-Specific Membrane Antigen, in Patients with Metastatic Prostate Cancer; J. Nucl. Med., 2012, vol. 53, No. 12, pp. 1883-1891.
Dapp et al., PEGylation, increasing specific activity and multiple dosing as strategies to improve the risk-benefit profile of targeted radionuclide therapy with 177Lu-DOTA-bombesin analogues; EJNMMI Research, 2012, vol. 2, No. 24, 12-pages.
Dumont et al., Targeted Radiotherapy of Prostate Cancer with a Gastrin-Releasing Peptide Receptor Antagonist Is Effective as Monotherapy and in Combination with Rapamycin; JNM SNM Journals; Feb. 25, 2020; 9-pages.
Eder et al., Preclinical Evaluation of a Bispecific Low-Molecular HeterodimerTargeting Both PSMAandGRPR for Improved PETImaging and Therapy of Prostate Cancer; The Postate, 2014, vol. 74; pp. 659-668.
Fang et al., Pm-149 DOTA bombesin analogs for potential radiotherapy In vivo comparison with Sm-153 and Lu-177 labeled DO3A-amide-Ala-BBN(7-14)NH2; Nuclear Medicine and Biology, vol. 29, 2002, pp. 423-430.
Garrison et al., In Vivo Evaluation and Small PET/CT of a Prostate Cancer Mouse Model Using 64Cu Bombesin Analogs: Side-by-Side Comparison of the CB-TE2A and DOTA Chelation Systems; JNM SNM Journals, Feb. 25, 2020, 12-pages.
Gourni et al., Structural Assessment and Biological Evaluation of Two N3S Bombesin Derivatives; Journal of Medicinal Chemistry; 13-pages.
Zhang et al., DOTA-PESIN, a DOTA-conjugated bombesin derivative designed for the imaging and targeted radionuclide treatment of bombesin receptor-positive tumours; Eur J. Nucl. Med. Mol. Imaging, 2007, vol. 34, pp. 1198-1208.
Holland et al., 89Zr-DFO-J591 for immunoPET imaging of prostate-specific membrane antigen (PSMA) expression in vivo; J. Nucl. Med., 2010, vol. 51, No. 8, pp. 1293-1300.
Jiang et al., 177Lu-labeled RGD-BBN heterodimeric peptide for targeting prostate carcinoma; Nuclear Medicine Communications; 6-pages.
Johnson et al., Evaluation of Combined 177Lu-DOTA-8-AOC-BBN(7-14)NH2 GRP Receptor Targeted Radiotherapy and Chemotherapy in PC-3 Human Prostate Tumor Cell Xenografted SCID Mice; Cancer Biother Radiopharm., 2006, vol. 21, No. 2, pp. 125-166.

(Continued)

*Primary Examiner* — D. L. Jones
(74) *Attorney, Agent, or Firm* — Stinson LLP

(57) ABSTRACT

Disclosed are compositions and methods relating to prostate cancer. In particular, disclosed are bivalent targeting ligands that specifically bind prostate specific membrane antigen and gastrin-releasing peptide receptor. Bivalent binding agents disclosed herein can be used to image a tissue in a subject in need thereof and to diagnose prostate cancer in a subject in need thereof. Bivalent binding agents disclosed herein can be used to treat prostate cancer in a subject in need thereof.

9 Claims, 10 Drawing Sheets

Specification includes a Sequence Listing.

(56) References Cited

OTHER PUBLICATIONS

Koumarianou et al., Comparative study on DOTA-derivatized bombesin analog labeled with 90Y and 177Lu: in vitro and in vivo evaluation; Nuclear Medicine and Biology, 2009, vol. 36, pp. 591-603.

Kozikowski et al., Synthesis of Urea-Based Inhibitors as Active Site Probes of Glutamate Carboxypeptidase II: Efficacy as Analgesic Agents; J. Med. Chem; 2004, vol. 47, pp. 1729-1739.

Lantry et al., 177Lu—AMBA: Synthesis and Characterization of a Selective 177Lu-Labeled GRP-R Agonist for Systemic Radiotherapy of Prostate Cancer; The Journal of Nuclear Medicine; 2006, vol. 47, No. 7, pp. 1144-1152.

Lears et al., In Vitro and In Vivo Evaluation of 64Cu-Labeled SarAr-Bombesin Analogs in Gastrin-Releasing Peptide Receptor—Expressing Prostate Cancer; J. Nucl. Med., 2011, vol. 52, No. 3, pp. 470-477.

Lolios et al., Novel Bispecific PSMA/GRPr Targeting Radioligands with Optimized Pharmacokinetics for Improved PET Imaging of Prostate Cancer; Bioconjugate Chemistry, 15-pages.

Maecke et al., 68Ga-Labeled Peptides in Tumor Imaging; JNM SNM Journals; Feb. 20, 2020; 8-pages.

Markwalder et al., Gastrin-releasing Peptide Receptors in the Human Prostate: Relation to Neoplastic Transformation; Cancer Research; 1999, vol. 59, pp. 1152-1159.

Mease et al., PET Imaging in Prostate Cancer: Focus on Prostate-Specific Membrane Antigen; Curr Top Med Chem., 2013, vol. 13, No. 8, pp. 951-962.

Morris et al., Phase I Evaluation of J591as a Vascular Targeting Agent in Progressive Solid Tumors; Cancer Therapy: Clinical; 8-pages.

Nock et al., Potent Bombesin-like Peptides for GRP-Receptor Targeting of Tumors with 99mTc: A Preclinical Study; J. Med. Chem, 2005, vol. 48, pp. 100-110.

Pandit-Taskar et al., Antibody mass escalation study in patients with castration resistant prostate cancer using 111I-J591: Lesion detectability and dosimetric projections for 90Y radioimmunotherapy; J. Nucl. Med., 2008, vol. 49, No. 7, pp. 1066-1074.

Pandit-Taskar et al., A Phase I/II Study for Analytic Validation of 89Zr-J591 ImmunoPET as a Molecular Imaging Agent for Metastatic Prostate Cancer; Clin Cancer Res., 2015, vol. 21, No. 23; pp. 5277-5285.

Perry et al., In Vitro and in Vivo Evaluation of 64Cu-Labeled DOTA-Linker-Bombesin(7-14) Analogues Containing Different Amino Acid Linker Moieties; Bioconjugate Chem., 2007, vol. 18, pp. 1110-1117.

Pillai et al. Radiolabeled enzyme inhibitors and binding agents targeting PSMA: Effective theranostic tools for imaging and therapy of prostate cancer; Nuclear Medicine and Biology; 30-pages.

Prasanphanich et al., [64Cu-NOTA-8-Aoc-BBN(7-14)NH2] targeting vector for positron-emission tomography imaging of gastrin-releasing peptide receptor-expressing tissues; PNAS, 2007, vol. 104, No. 30, pp. 12462-12467.

Rowe et al., Prostate-Specific Membrane Antigen—Targeted Radiohalogenated PET and Therapeutic Agents for Prostate Cancer; The Journal of Nuclear Medicine, 2016, vol. 57, No. 10 (Suppl.3); 7-pages.

Scopinaro et al., 99mTc-bombesin detects prostate cancer and invasion of pelvic lymph nodes; Eur J. Nucl Med Mol Imaging, 2003, vol. 30, pp. 1378-1382.

Smith et al., Radiochemical investigations of 177Lu-DOTA-8-AOC-BBN[7-14]NH2: an in vitro/in vivo assessment of the targeting ability of this new radiopharmaceutical for PC-3 human prostate cancer cells; Nuclear Medicine and Biology, 2003, vol. 30, pp. 101-109.

Smith et al., Radiochemical Investigations of Gastrin-releasing Peptide Receptor-specific [99mTc(X)(CO)3-Dpr-Ser-Ser-Ser-Gln-Trp-Ala-Val-Gly-l-lis-Leu-Met-(NH2)] in PC-3, Tumor-bearing, Rodent Models: Syntheses, Radiolabeling, and in Vitro/in Vivo Studies where Dpr 2,3-Diaminopropionic acid and X H2O or P(CH2OH)13; Cancer Research 63, p2003; p. 4082-4088.

Smith et al., Gastrin releasing peptide (GRP) receptor targeted radiopharmaceuticals: A concise update; Nuclear Medicine and Biology 30 (2003), pp. 861-868.

University of Missouri Biomedical & Health Sciences Technologies, 8-pages.

Vallabhajosula et al., Pharmacokinetics and Biodistribution of 111Inand 177Lu-Labeled J591 Antibody Specific for Prostate-Specific Membrane Antigen: Prediction of 90Y-J591 Radiation Dosimetry Based on 111In or 177Lu?; JNM SNM Journals, 9-pages.

Van De Wiele et al., Technetium-99m RP527, a GRP analogue for visualisation of GRP receptor-expressing malignancies: a feasibility study; 6-pages.

Van Der Lely et al., Octreoscan Radioreceptor Imaging; Endocrine, 2003; vol. 20, No. 3, pp. 307-311.

Van De Wiele et al., Biodistribution and Dosimetry of 99mTc-RP527, a Visualization of GRP Receptor—Expressing Malignancies; JNM SNM Journals, 7-pages.

Yang et al., Comparative in vitro and in vivo evaluation of two 64Cu-labeled bombesin analogs in a mouse model of human prostate adenocarcinomaNuclear; Medicine and Biology, 2006, vol. 33, pp. 371-380.

Zhang et al., Synthesis and Evaluation of Bombesin Derivatives on the Basis of Pan-Bombesin Peptides Labeled with Indium-111, Lutetium-177, and Yttrium-90 for Targeting Bombesin Receptor-Expressing Tumors; Cancer Research, 2004, vol. 64, pp. 6707-6715.

\* cited by examiner

DUPA-6-Ahx-Lys(DOTA)-6-Ahx-RM2

DUPA-6-Ahx-Lys(DOTA)-6-Ahx-RM2

```
                         SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (1)..(1)
<223> OTHER INFORMATION: DOTA amino-1-carboxymethyl-piperidine linked to
      D-Phenylalanine
<220> FEATURE:
<221> NAME/KEY: MISC_FEATURE
<222> LOCATION: (8)..(8)
<223> OTHER INFORMATION: Statin (4-amino-3-hydroxy-6-methylheptanoic
      acid)

<400> SEQUENCE: 1

Phe Gln Trp Ala Val Gly His Xaa Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (1)..(1)
<223> OTHER INFORMATION: DOTA-p-aminomethylaniline-diglycolic acid
      linked to D-Phenylalanine

<400> SEQUENCE: 2

Phe Gln Trp Ala Val Gly His Leu
1               5
```

DUAL TARGETING LIGAND FOR CANCER DIAGNOSIS AND TREATMENT

CROSS-REFERENCE TO RELATED APPLICATIONS

This application claims priority to U.S. Provisional Application Ser. No. 62/779,623, filed on Dec. 14, 2018, the disclosure of which is hereby incorporated by reference in its entirety.

STATEMENT REGARDING FEDERALLY SPONSORED RESEARCH OR DEVELOPMENT

This invention was made with government support under VA Merit Application 1I01BX003392. The government of the United States has certain rights in the invention.

INCORPORATION OF SEQUENCE LISTING

A paper copy of the Sequence Listing and a computer readable form of the Sequence Listing containing the file named "17UMC001_ST25.txt", which is 1,150 bytes in size (as measured in MICROSOFT WINDOWS® EXPLORER), are provided herein and are incorporated herein by reference. This Sequence Listing consists of SEQ ID NOS:1-2.

BACKGROUND OF THE DISCLOSURE

The present disclosure is directed to compositions and methods relating to prostate cancer. More particularly, the present disclosure is directed to bivalent binding agents that specifically bind prostate specific membrane antigen and gastrin-releasing peptide receptor. Also disclosed are methods for imaging tissues and for diagnosing prostate cancer using binding agents that specifically bind prostate specific membrane antigen and gastrin-releasing peptide receptor.

Prostate cancer (PCa) is the second leading cause of cancer-related death in men. Detection of prostate tumors at an initial stage continues to be challenging for oncologists and is of great clinical importance. Current treatment methods for PCa include radiation therapy, chemotherapy, surgery, hormonal therapy, photodynamic therapy, and combination therapy. The selection of a treatment generally varies depending on the stage of the disease. Unfortunately, none of these therapies is highly effective against metastatic disease, and, each has inherent disadvantages that patients oftentimes decline from during their use. While localized PCa can be treated by removal of malignant tissue, radical prostatectomy may result in loss of urinary control and impotence. Radiation therapy can also cause rectal bleeding and increased risk of colon and bladder cancer. Therefore, treatment of invasive or metastatic PCa is often limited to palliative hormonal therapy and/or chemotherapy. Advanced stages of PCa can also significantly impact quality of life due to bone disintegration, pain, and obstruction of urination among other disorders. 2020 projections, based on increasing prevalence of PCa, indicate that the cost for treating/detecting PCa will rise to $16 billion in the US. The high economic burden of PCa has also been predicted from a model analysis of the Surveillance Epidemiology and End Results (SEER) database that estimated a lifetime cost of $110,520 (95% CI: US $110,324-110,739) per patient. The current methods of clinical identification for prostate cancer patients are considered insufficient for early diagnosis.

Prostate specific membrane antigen (PSMA) is a type II, integral membrane glycoprotein with an extensive extracellular domain (44-750 amino acids) and plays a significant role in prostate carcinogenesis and progression. PSMA is named largely due to its higher level of expression on prostate cancer cells; however, its particular function on prostate cancer cells remains unresolved. PSMA is overexpressed in the malignant prostate tissues when compared to other organs in the human body such as kidney, proximal small intestine, and salivary glands. The ability of PSMA to be rapidly internalized coupled with a high incidence of expression on various tumor neovasculature including prostate cancer, has recently led to the design and development of new radioactive diagnostic and therapeutic agents targeting PSMA as a clinical biomarker for early detection, staging, and potential treatment of human disease.

The two main categories for the design of new PSMA-targeted radioimaging agents are antibodies and small molecule inhibitors. The more-widely studied antibody is J591, which reacts with an extracellular epitope of PSMA. J591 has been labeled with $^{111}$In for SPECT imaging and $^{89}$Zr for PET imaging, and evaluated in tumor-bearing mice. Clinical studies of $^{111}$In-labeled J591 have been performed to evaluate scintigraphic imaging efficacy and to estimate dosimetry for $^{90}$Y radioimmunotherapy. A Phase I/II trial of 50 patients receiving the $^{89}$Zr-labeled antibody (J591) showed that bony metastases and soft tissue lesions could be readily detected, proving superior to conventional imaging modalities.

Small molecules typically inhibit the zinc-cofactor enzymatic site of PSMA. These zinc-binding molecules are either phosphorus, thiol, or urea conjugates attached to a glutamate moiety. In particular, the urea DUPA (2-[3-(1,3-dicarboxypropyl)-ureido]pentanedioic acid) has been coupled to a wide variety of molecules for radiolabeling with $^{18}$F, $^{64}$Cu, $^{68}$Ga, and $^{86}$Y. Of these, $^{18}$F-DCFBC ((S)-2-(3-(R)-1-carboxy-2(methylthio)ethyl)ureido)pentanedioc acid), $^{68}$Ga-HBED-CC (N,N'-bis[2-hydroxy-5-(carboxyethyl)-benzyl]ethylenediamine-N,N'-diacetic acid), and BAY1075553, have shown promising results for PET imaging in clinical studies to stage and restage prostate cancer, as well as to detect metastatic disease.

The gastrin-releasing peptide receptor (GRPR) is overexpressed in a variety of human tumors and is present in a high percentage of prostate cancers. The GRPR is a subtype of the bombesin (BBN) receptor superfamily found to be expressed in several human cancers, such as prostate, colon, breast, and pancreatic cancer. Many of these cancers are targeted with radiolabeled BBN or RM2 derivatives for site-directed molecular imaging or therapy. BBN, a tetradecapeptide analogue of human GRP, has very high binding affinity for GRPR and numerous BBN analogues have been synthesized and characterized for GRPR-positive tumor-targeted imaging and therapy. RM2 (DOTA amino-1-carboxymethyl-piperidine-D-Phe-Gln-Trp-Ala-Val-Gly-His-Sta-Leu-NH$_2$) (SEQ ID NO: 1) is an antagonist analogue of BBN that has recently been shown to have improved uptake and retention in tumors as compared to agonist GRPR-targeting ligands.

Gallium-68-labeled RM2 has been evaluated in 7 men with recurrent prostate cancer and compared to the agonist $^{68}$Ga-PSMA-11 (Glu-NH—CO—NH-Lys-(Ahx)-(HBED-CC), where Ahx=6-aminohexanoic acid). While PSMA-11 had high uptake in the salivary glands and small intestine, with both hepatic and renal clearance, RM2 had the highest uptake in the pancreas and was excreted predominately in the urine. Because of the differences in biodistribution, $^{68}$Ga-PSMA-11 and $^{68}$Ga-RM2 detected different lymph nodes: $^{68}$Ga-PSMA-11 more conspicuously in the lower abdomen, and $^{68}$Ga-RM2 more conspicuously in the upper abdomen and thorax. A $^{64}$Cu-labeled, PEGylated derivative of RM2, $^{64}$Cu-CB-TE2A-AR06, has also been studied in newly diagnosed PCa patients. This conjugate cleared rapidly through the kidneys, enabling high contrast imaging of prostate tumors in ¾ men. Maina et al. developed the peptide SB3 (DOTA-p-aminomethylaniline-diglycolic acid-DPhe-Gln-Trp-Ala-Val-Gly-His-Leu-NHEt) (SEQ ID NO:2), and the $^{68}$Ga-labeled agent detected metastatic disease in 5/9 patients.

Accordingly, novel diagnostic techniques for early detection and staging of primary or metastatic prostate cancer disease are warranted.

BRIEF DESCRIPTION OF THE DISCLOSURE

In one aspect, the present disclosure is directed to a bivalent binding agent of formula (I) [DUPA-6-Ahx-Lys(DOTA)-X-RM2] (I) wherein X is selected from the group consisting of 5-aminovaleric acid (5-Ava), 6-amino hexanoic acid (6-Ahx), 8-aminooctanoic acid) (8Aoc), and paraamino benzoic acid (AMBA).

In one aspect, the present disclosure is directed to a bivalent binding agent of formula (II) [DUPA-6-Ahx-Lys(M-DOTA)-X-RM2] (II) wherein X is selected from 5-aminovaleric acid (5-Ava), 6-amino hexanoic acid (6-Ahx), 8-aminooctanoic acid) (8Aoc), and paraamino benzoic acid (AMBA); and wherein M is selected from Gallium (Ga), Indium (In), Lutetium (Lu), Yttrium (Y), Samarium (Sm), Promethium (Pm), $^{67}$Ga, $^{68}$Ga, $^{111}$In, $^{177}$Lu, $^{90}$Y, $^{86}$Y, $^{153}$Sm, and $^{149}$Pm.

In another aspect, the present disclosure is directed to a method of imaging a tissue in a subject in need thereof, the method comprising: administering to the subject a bivalent binding agent of formula (II) [DUPA-6-Ahx-Lys(M-DOTA)-X-RM2] (II) wherein X is selected from 5-aminovaleric acid (5-Ava), 6-amino hexanoic acid (6-Ahx), 8-aminooctanoic acid) (8Aoc), and paraamino benzoic acid (AMBA); and wherein M is selected from $^{67}$Ga, $^{68}$Ga, $^{111}$In, $^{86}$Y, and $^{177}$Lu; and applying an imaging technique to detect emitted gamma rays.

In another aspect, the present disclosure is directed to a method of diagnosing prostate cancer in a subject having or suspected of having prostate cancer, the method comprising: administering to the subject a bivalent binding agent of formula (II) [DUPA-6-Ahx-Lys(M-DOTA)-X-RM2] (II) wherein X is selected from 5-aminovaleric acid (5-Ava), 6-amino hexanoic acid (6-Ahx), 8-aminooctanoic acid) (8Aoc), and paraamino benzoic acid (AMBA); and wherein M is selected from $^{67}$Ga, $^{68}$Ga, $^{111}$In, $^{86}$Y, and $^{177}$Lu; applying an imaging technique to detect emitted gamma rays; and diagnosing the subject as having prostate cancer based on uptake of the bivalent binding agent as detected in the imaging of the subject.

In another aspect, the present disclosure is directed to a method of treating prostate cancer in a subject having or suspected of having prostate cancer, the method comprising: administering to the subject a bivalent binding agent of formula (II) [DUPA-6-Ahx-Lys(M-DOTA)-X-RM2] (II) wherein X is selected from 5-aminovaleric acid (5-Ava), 6-amino hexanoic acid (6-Ahx), 8-aminooctanoic acid) (8Aoc), and paraamino benzoic acid (AMBA); and wherein M is selected from $^{177}$Lu, $^{90}$Y, $^{153}$Sm, and $^{149}$Pm.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings wherein.

DETAILED DESCRIPTION

Figure 1:
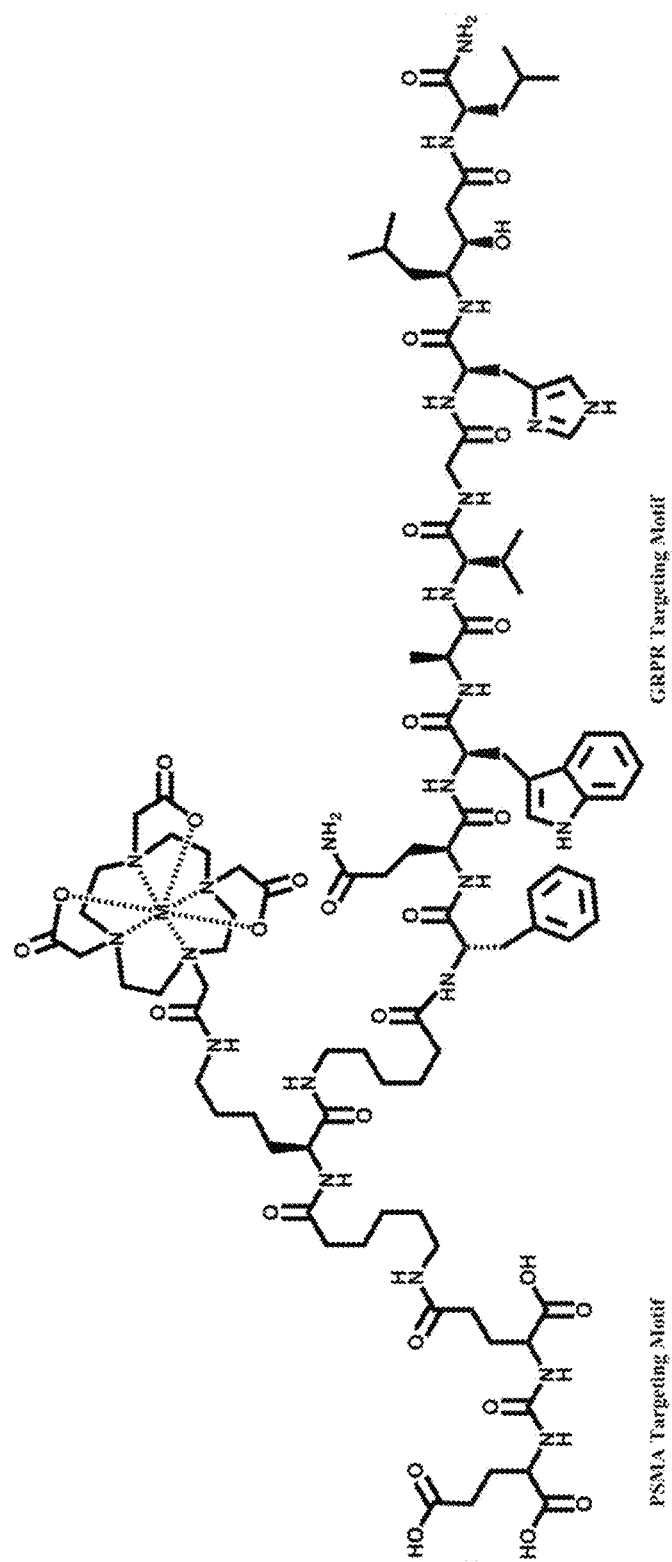
FIG. 1 depicts the chemical structure of metallated [DUPA-6-Ahx-Lys(M-DOTA)-6-Ahx-RM2] conjugate.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used in this application, including the appended claims, the singular forms "a," "an," and "the" include plural references, unless the content clearly dictates otherwise, and are used interchangeably with "at least one" and "one or more."

Disclosed are compositions and methods relating to prostate cancer. Bivalent binding agents disclosed herein specifically bind prostate specific membrane antigen and gastrin-releasing peptide receptor. Bivalent binding agents disclosed herein can be used to image a tissue in a subject in need thereof. Bivalent binding agents disclosed herein can also be used to diagnose prostate cancer in a subject having or suspected of having prostate cancer.

In one aspect, the present disclosure is directed to a bivalent binding agent of formula (I):

[DUPA-6-Ahx-Lys(DOTA)-X-RM2]        (I)

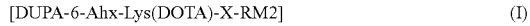

wherein X is selected from 5-aminovaleric acid (5-Ava), 6-amino hexanoic acid (6-Ahx), 8-aminooctanoic acid) (8Aoc), and paraamino benzoic acid (AMBA).

DOTA (1,4,7,10-tetraazacyclododecane-1,4,7,10-tetraacetic acid)) is used as a complexing agent with high affinity for di- and trivalent cations. DUPA (2-[3-(1,3-dicarboxypropyl)-ureido]pentanedioic acid) is a small-molecule that specifically binds to prostate specific membrane antigen (PSMA). RM2 (D-Phe-Gln-Trp-Ala-Val-Gly-His-Sta-Leu-NH2) (SEQ ID NO:1) is an antagonist analogue of bombesin (BBN) peptide that specifically binds to gastrin-releasing peptide receptor (GRPR).

In one aspect, the present disclosure is directed to a bivalent binding agent of formula (II):

[DUPA-6-Ahx-Lys(M-DOTA)-X-RM2]        (II).

Suitably, X is selected from 5-Ava, 6-Ahx, 8Aoc, and AMB. Suitably, M is selected from Gallium (Ga), Indium (In), Lutetium (Lu), Yttrium (Y), Samarium (Sm), Promethium (Pm), $^{67}$Ga, $^{68}$Ga, $^{111}$In, $^{177}$Lu, $^{90}$Y, $^{86}$Y, $^{153}$Sm, and $^{149}$Pm.

Gallium- (Ga), Indium- (In), Yttrium- (Y), and Lutetium (Lu)-labeled radio-pharmaceuticals each have a half-life, decay mode and emission profile suitable for imaging. The beta emission of $^{177}$Lu also renders it useful as a therapeutic radionuclide. $^{111}$In is a cyclotron-produced radionuclide via the (p,2n) reaction and decays mainly by electron capture, producing two gamma photons (171 keV and 245 keV) which fall into a suitable range for imaging purposes. A physical half-life of 2.8 days also makes $^{111}$In suitable for molecular imaging. For example, since it is readily available, it can be procured within a reasonable timeframe to allow for drug preparation, quality control, drug delivery, and molecular imaging investigations (preclinical or clinical). As a reactor-produced product, $^{177}$Lu can be obtained in a high specific activity/carrier-free state from a $^{176}$Yb target via indirect neutron capture (gamma) as to avoid the presence of long-lived, high-energy, metastable isotopes. However, it is most regularly synthesized in moderate specific activity via direct neutron capture using a $^{176}$Lu-enriched target. In addition to the two gamma photons that are suitable for imaging (113 keV and 208 keV), $^{177}$Lu also emits a beta particle with an energy of 498 keV that can achieve a tissue penetration depth of ~2 mm, making it suitable for use with smaller size tumors. The 6.7 day physical half-life makes it suitable for use as a diagnostic or therapeutic peptide-based cell targeting agent with a longer in vivo biological half-life. $^{68}$Ga also possesses ideal nuclear characteristics for PET molecular imaging. As a radionuclide produced by the elution of parent $^{68}$Ge in a radionuclide generator, $^{68}$Ga decays by positron emission [Eβ+ max=1.899 MeV (89%)]. It has a half-life of 68 minutes, which is also sufficiently long for drug preparation, quality control, drug delivery, drug clearance, and patient imaging. However, the half-life of $^{68}$Ga may not be sufficiently long enough for in vivo investigations at later time-points. As a result, $^{67}$Ga can used as a substitute due to its extended half-life of 78.26 hours. $^{67}$Ga is also produced via a cyclotron. Charged particle bombardment of enriched $^{68}$Zn is used to produce $^{67}$Ga. The half-life of $^{67}$Ga is 78 hours. It decays by electron capture, then emits de-excitation gamma rays (93, 185, 288, 394 KeV energy) that are detected by a gamma camera. $^{177}$Lu, $^{111}$In, and $^{67}$Ga lend themselves well to successful, inert chelation within the DOTA bifunctional chelator as a result of their inherent chemical properties, such as 3+ oxidation states, hard metal centers, and larger-sized ionic radii. $^{86}$Y is suitable for imaging uses and $^{90}$Y is suitable for therapeutic uses.

In one aspect, the present disclosure is directed to a method of imaging a tissue in a subject in need thereof. The method includes administering to a subject in need thereof a bivalent binding agent of formula (II)

[DUPA-6-Ahx-Lys(M-DOTA)-X-RM2]          (II).

Suitably, X is selected from 5-Ava, 6-Ahx, 8Aoc, and AMB. Suitably, M is selected from $^{67}$Ga, $^{68}$Ga, $^{111}$In, $^{86}$Y, and $^{177}$Lu. The method further includes applying an imaging technique to detect emitted gamma rays.

Suitable imaging techniques include positron-emission tomography (PET) and single photon emission computed tomography (SPECT). Positron-emission tomography (PET) is a nuclear medicine imaging technique that detects pairs of gamma rays emitted indirectly by a positron-emitting radioligand that is introduced into the body of a subject. Three-dimensional images of tracer concentration within the body are then constructed by computer analysis. Singlephoton emission computed tomography (SPECT, or less commonly, SPET) is a nuclear medicine tomographic imaging technique directly detecting gamma rays emitted by a radionuclide that is introduced into the body of a subject. SPECT imaging is performed by using a gamma camera to acquire multiple 2-D images (also called projections), from multiple angles. A computer is then used to apply a tomographic reconstruction algorithm to the multiple projections, yielding a 3-D data set. This data set may then be manipulated to show thin slices along any chosen axis of the body.

As used herein, "subject in need thereof" (also used interchangeably herein with "a patient in need thereof") refers to a subject susceptible to or at risk of a specified disease, disorder, or condition. The methods disclosed herein can be used with a subset of subjects who are susceptible to or at elevated risk for prostate cancer. Because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions. Formulations of the present disclosure can be administered to "a subject in need thereof". As used herein, "a subject" (also interchangeably referred to as "an individual" and "a patient") refers to animals including humans and non-human animals. Accordingly, the compositions and methods disclosed herein can be used for human and veterinary medical applications. Suitable subjects include warm-blooded mammalian hosts, including humans, companion animals (e.g., dogs, cats), cows, horses, mice, rats, rabbits, primates, and pigs.

Suitable methods for administration of formulations of the present disclosure are by parenteral (e.g., intravenous (IV)) routes or orally, and the formulations administered ordinarily include effective amounts of product in combination with acceptable diluents, carriers and/or adjuvants.

In one aspect, the present disclosure is directed to a method of diagnosing prostate cancer in a subject having or suspected of having prostate cancer. The method includes administering to a subject having, or suspected of having, prostate cancer a bivalent binding agent of formula (II)

[DUPA-6-Ahx-Lys(M-DOTA)-X-RM2]          (II).

Suitably, X is selected from 5-Ava, 6-Ahx, 8Aoc, and AMBA. Suitably, M is selected from $^{67}$Ga, $^{68}$Ga, $^{111}$In, $^{86}$Y, and $^{177}$Lu. The method further includes applying an imaging technique to detect emitted gamma rays. A subject is diagnosed as having prostate cancer based on uptake of the bivalent binding agent as detected in PET or SPECT imaging of the subject. Further, a positive correlation of the bivalent binding agent uptake in a tumor by physiological PET or SPECT investigations and anatomical computerized tomography (CT) scan or magnetic resonance imaging (MRI) scan can further confirm the diagnosis.

Suitable imaging techniques include positron-emission tomography (PET) and single photon emission computed tomography (SPECT), as described herein.

In one aspect, the present disclosure is directed to a method of treating prostate cancer in a subject having or suspected of having prostate cancer, the method comprising: administering to the subject a bivalent binding agent of formula (II) [DUPA-6-Ahx-Lys(M-DOTA)-X-RM2] (II) wherein X is selected from 5-aminovaleric acid (5-Ava), 6-amino hexanoic acid (6-Ahx), 8-aminooctanoic acid) (8Aoc), and paraamino benzoic acid (AMBA); and wherein M is selected from $^{177}$Lu, $^{90}$Y, $^{153}$Sm, and $^{149}$Pm.

As used herein, "a subject in need thereof" refers to a subject susceptible to or at risk of a specified disease, disorder, or condition. More particularly, in the present disclosure the methods of treating prostate cancer is to be used with a subset of subjects who are susceptible to or at elevated risk for experiencing prostate cancer. Such subjects may include, but are not limited to, subjects susceptible to or at elevated risk of prostate cancer. Subjects may be susceptible to or at elevated risk for prostate cancer due to family history, age, environment, and/or lifestyle. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions. As used herein, "susceptible" and "at risk" refer to having little resistance to a certain disease, disorder or condition, including being genetically predisposed, having a family history of, and/or having symptoms of the disease, disorder or condition.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient; the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles. Illustrative formats for oral administration include tablets, capsules, elixirs, syrups, and the like. Illustrative routes for parenteral administration include intravenous, intraarterial, intraperitoneal, epidurial, intraurethral, intrasternal, intramuscular and subcutaneous, as well as any other art recognized route of parenteral administration.

Depending upon the disease as described herein, the route of administration and/or whether the compounds and/or compositions are administered locally or systemically, a wide range of permissible dosages are contemplated herein, including doses of about 100 μg/70 kg or less. The dosages may be single or divided, and may be administered according to a wide variety of protocols, including q.d., b.i.d., t.i.d., or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

The effective use of the compounds, compositions, and methods described herein for treating or ameliorating one or more effects of prostate cancer using one or more compounds described herein may be based upon animal models, such as murine, canine, porcine, and non-human primate animal models of disease. For example, it is understood that prostate cancer in humans may be characterized by a loss of function, and/or the development of symptoms, each of which may be elicited in animals, such as mice, and other surrogate test animals. In particular the mouse model described herein, may be used to evaluate the methods of treatment and the pharmaceutical compositions described herein to determine the therapeutically effective amounts described herein.

The following examples further illustrate specific embodiments of the invention; however, the following illustrative examples should not be interpreted in any way to limit the invention.

EXAMPLES

Example 1

Commercially-available chemical reagents were purchased from Chem-Impex International (Wood Dale, Ill.) and Fisher Scientific (Waltham, Mass.) and used without further purification. Amino acid residues and resins for solid-phase and manual peptide synthesis were purchased from Novabiochem/EMD Biosciences, Inc. (La Jolla, Calif.) and Advanced ChemTech (Louisville, Ky.). Electrospray-ionization (ESI-MS) and Matrix Assisted Laser Desorption Ionization (MALDI) mass spectrometry, for characterization of the peptide precursor, conjugate, and metallated conjugates were performed at the MS Facility, University of Missouri (Columbia, Mo.). PC-3 and LNCaP cells were obtained from American Type Culture Collection and were maintained by the University of Missouri Cell and Immunobiology Core Facility (Columbia, Mo.). Reversed-phase High-Performance Liquid Chromatography (RP-HPLC) analyses of compounds were performed on a Shimadzu SCL-10A system (Shimadzu, Kyoto, Japan) equipped with a Shimadzu SPD-10A UV-vis tunable absorbance detector ($\lambda=280$ nm), an Eppendorf TC-50 column heater (Eppendorf, Hamburg, Germany).

Reversed-Phase High-Performance Liquid Chromatography (RP-HPLC)

Purification of [DUPA-6-Ahx-Lys-6-Ahx-RM2] and [DUPA-6-Ahx-Lys(DOTA)-6-Ahx-RM2] conjugate was performed on a semi-preparative, reversed-phase C18 column (Phenomenex Jupiter Proteo, 250×10.00 mm, 10 µm; Phenomenex, Torrance, Calif.). Purification of [DUPA-6-Ahx-Lys($^{nat/*}$M-DOTA)-6-Ahx-RM2], where M=$^{nat/67}$Ga, $^{nat/111}$In, $^{nat/177}$Lu=natural/radioisotopic gallium, indium, and lutetium conjugates, was performed on an analytical, reversed-phase C18 column (Phenomenex Jupiter Proteo, 250×4.60 mm, 5 µm). The solvent system consisted of ultrapure water containing 0.1% trifluoroacetic acid (Solvent A) and acetonitrile containing 0.1% trifluoroacetic acid (Solvent B). A linear gradient of 70:30A/B to 40:60A/B gradient over 15 min (followed by an additional 10 min at 5:95A/B) was used to purify the peptides and metallated constructs. Flow rates of 5 mL/min for the semipreparative and 1.5 mL/min for the analytical RP-HPLC were used during purification procedures. Purified peptide conjugates were lyophilized in a CentriVap system (Labconco, Kansas City, Mo., USA).

Chemistry

Synthesis of the PSMA-Targeting, Small-Molecule, DUPA

Synthesis of 2-[3-(1,3-Bis-tert-butoxycarbonylpropyl)-ureido]pentanedioic acid 1-tert-butyl ester (DUPA precursor) was prepared according to a published procedure with only slight modification [57]. Triethyl amine (2.0 mL, 16.38 mmol) was added to a solution of L-glutamate di-tert-butyl ester hydrochloride (2.0 g, 6.78 mmol) and triphosgene (659.6 mg, 2.24 mmol) in methylene chloride (55.0 mL) and stirred for 2 h at −78° C. under a nitrogen atmosphere. After stirring, a methylene chloride solution (10.0 mL) containing L-Glu (OBn-OtBu) (2.4 g, 7.44 mmol) and triethyl amine (1.2 mL, 9.82 mmol) was added. The reaction mixture was allowed to come to room temperature over a one hour time-period, and the solution continued to stir overnight. The reaction was quenched with 1.0 M HCl, and the organic layer was washed with brine and dried over $Na_2SO_4$. The crude product was purified using flash chromatography (Hexane:Ethyl Acetate, 1:1) to produce a colorless oil that was recrystallized from a mixture of hexane and methylene chloride. Compounds 2-[3-(3-Benzyloxycarbonyl-1-tert-butoxycarbonyl-propyl)-ureido]pentanedioic acid) di-tert-butyl ester were characterized by $^1$H and $^{13}$C nuclear magnetic resonance (NMR) spectroscopy and characterized by ESI-MS ($C_{30}H_{47}N_2O_9$: Calculated, 578.3184; Found, 579.3289). Deprotection of the benzyl group was performed by hydrogenation. Ten percent palladium on carbon (Pd/C) was added to a solution of 2-[3-(3-Benzyloxycarbonyl-1-tert-butoxycarbonyl-propyl)-ureido]pentanedioic acid) di-tert-butyl ester (2 g, 3.45 mmol) in methylene chloride. The reaction mixture was hydrogenated at 1 atm for a period of 24 h at room temperature, after which the Pd/C was filtered through a celite pad and washed with methylene chloride. The crude product was purified using flash chromatography (Hexane:Ethyl Acetate, 0.4:0.6) to produce 2-[3-(1,3-Bis-tert-butoxycarbonylpropyl)-ureido]pentanedioic acid 1-tert-butyl ester as a colorless oil (1.35 g, 80.2%). The purified product was characterized by $^1$H and $^{13}$C NMR spectroscopy and characterized by ESI-MS ($C_{23}H_{41}N_2O_9$: Calculated, 488.2812; Found, 489.2808).

Direct Synthesis of [DUPA-6-Ahx-Lys(DOTA)-6-Ahx-RM2] Conjugate

The bivalent, PSMA/GRPR targeting precursor [DUPA-6-Ahx-Lys-6-Ahx-RM2], was prepared by direct stepwise synthesis using a manual, resin-based solid phase peptide synthesis employing traditional F-moc chemistry as shown in Scheme 1 (FIGS. 5A-5D). Briefly, Rink Amide-MBHA resin (0.1 mmol) and Fmoc protected amino acids with appropriate side-chain protections (0.2 mmol) were utilized for synthesis. The resin was swollen using a combination of methylene chloride (5 mL) and dimethyl formamide (DMF, 5 mL). A solution of 20% piperidine in DMF (4×4 mL) was added to the resin and nitrogen was bubbled through it for 5 min. The resin was washed with DMF (4×5 mL) and isopropyl alcohol (iPrOH, 3×3 mL). Formation of the free, N-terminal, primary amine was assessed by the Kaiser Test. Upon swelling the resin once again in DMF, a solution of Fmoc-Leu-OH (0.2 mmol), O-Benzotriazole-N,N,N',N'-tetramethyl-uronium-hexafluorophosphate (HBTU)(0.2 mmol), Hydroxybenzotriazole (HOBt) (0.2 mmol) and N,N Diisopropylethylamine (DIPEA) (0.4 mmol) in DMF was added to the resin/DMF solution. The resin was bubbled under helium gas for 5 h, after which it was washed with DMF (3×5 mL) and i-PrOH, (3×4 mL). The coupling efficiency was assessed by the Kaiser Test, and the above coupling procedure was repeated 12 additional times to produce the bivalent ligand precursor. Each coupling procedure took ~4-8 h. A cocktail of water, triisopropylsilane (TIS), and trifluoracetic acid (TFA) in a ratio of 2.5:2.5:95 was used to cleave the peptide from the resin, followed by peptide precipitation in methyl-t-butyl ether. The purified peptide/small molecule precursor [DUPA-6-Ahx-Lys)-6-Ahx-RM2] was obtained in ~60% yield after purification by RP-HPLC. Solvents were removed in vacuo using a Speed- Vac concentrator (Labconco, Kansas City, Mo.). The purified peptide precursor was characterized by MALDI-TOF mass spectrometry (Table 1).

TABLE 1

Matrix assisted laser desorption ionization (MALDI)-TOF mass spectrometry values for DUPA-6-Ahx-Lys-6-Ahx-RM2, DUPA-6-Ahx-Lys(DOTA)-6-Ahx-RM2 and metallated DUPA-6-Ahx-Lys(M-DOTA)-6-Ahx-RM2 conjugates. M is defined as $^{nat/67}Ga$, $^{nat/111}In$, $^{nat/177}Lu$.

| Analog | Mol. Formula | Calculated | Observed | HPLC tr (min) |
|---|---|---|---|---|
| DUPA-6-Ahx-Lys-6-Ahx-RM2 | $C_{84}H_{128}N_{20}O_{22}$ | 1768.95 | 1769.97 | 9.0 |
| DUPA-6-Ahx-Lys(DOTA)-6-Ahx-RM2 | $C_{100}H_{154}N_{24}O_{29}$ | 2155.11 | 2156.13 | 9.8 |
| DUPA-6-Ahx-Lys($^{nat}$Ga-DOTA)-6-Ahx-RM2 | $C_{100}H_{154}N_{24}O_{29}{}^{nat}Ga$ | 2223.03 | 2224.01 | 9.2 |
| DUPA-6-Ahx-Lys($^{nat}$In-DOTA)-6-Ahx-RM2 | $C_{100}H_{154}N_{24}O_{29}{}^{nat}In$ | 2267.88 | 2268.74 | 9.3 |
| DUPA-6-Ahx-Lys($^{nat}$Lu-DOTA)-6-Ahx-RM2 | $C_{100}H_{154}N_{24}O_{29}{}^{nat}Lu$ | 2327.60 | 2328.58 | 9.3 |
| DUPA-6-Ahx-Lys($^{67}$Ga-DOTA)-6-Ahx-RM2 | | | | 9.2 |
| DUPA-6-Ahx-Lys($^{111}$In-DOTA)-6-Ahx-RM2 | | | | 9.3 |
| DUPA-6-Ahx-Lys($^{177}$Lu-DOTA)-6-Ahx-RM2 | | | | 9.3 |

DOTA-NHS ester, 2,2',2"-(10-(2-((2,5-dioxopyrrolidin-1-yl)oxy)-2-oxoethyl)-1,4,7,10-tetraazacyclododecane-1,4,7-triyl)triacetic acid, was conjugated as the final step in the synthetic procedure via an active ester onto the ε-amine of the lysine residue of the bivalent peptide precursor [DUPA-6-Ahx-Lys-6-Ahx-RM2] to produce [DUPA-6-Ahx-Lys(DOTA)-6-Ahx-RM2], using a slightly-modified procedure that is similar to what has previously been described [49]. Briefly, DOTA-NHS (29 μmol) was stirred at room temperature in 200 μL of 0.1 M sodium phosphate buffer (pH=7.0). [DUPA-6-Ahx-Lys-6-Ahx-RM2] (2.9 μmol) was dissolved in 0.1 M sodium phosphate buffer and the pH was adjusted to 7.4 using 10% NaOH. The reaction mixture was allowed to stir for 6 h at 5-10° C., after which it was allowed to stir overnight at ambient temperature. The bivalent DOTA conjugate was purified by RP-HPLC and obtained in ~35% yield. MALDI-TOF mass spectrometry was used to confirm the identity of the new bivalent conjugate (Table 1).

Modified Synthesis of [DUPA-6-Ahx-Lys(DOTA)-6-Ahx-RM2] Conjugate

Figure 6A:
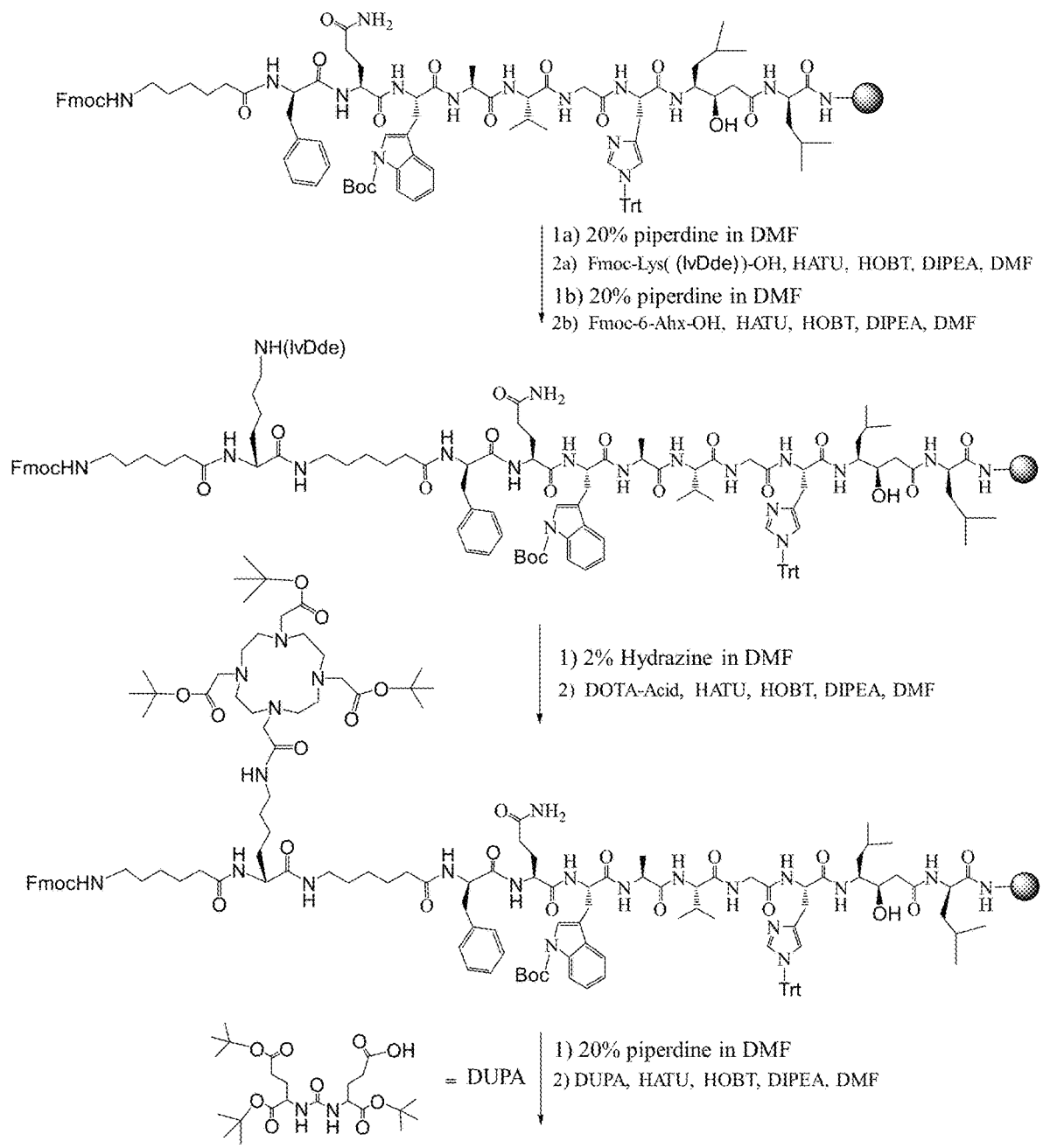
FIGS. 6A and 6B depict synthetic scheme 2.
Figure 6B:
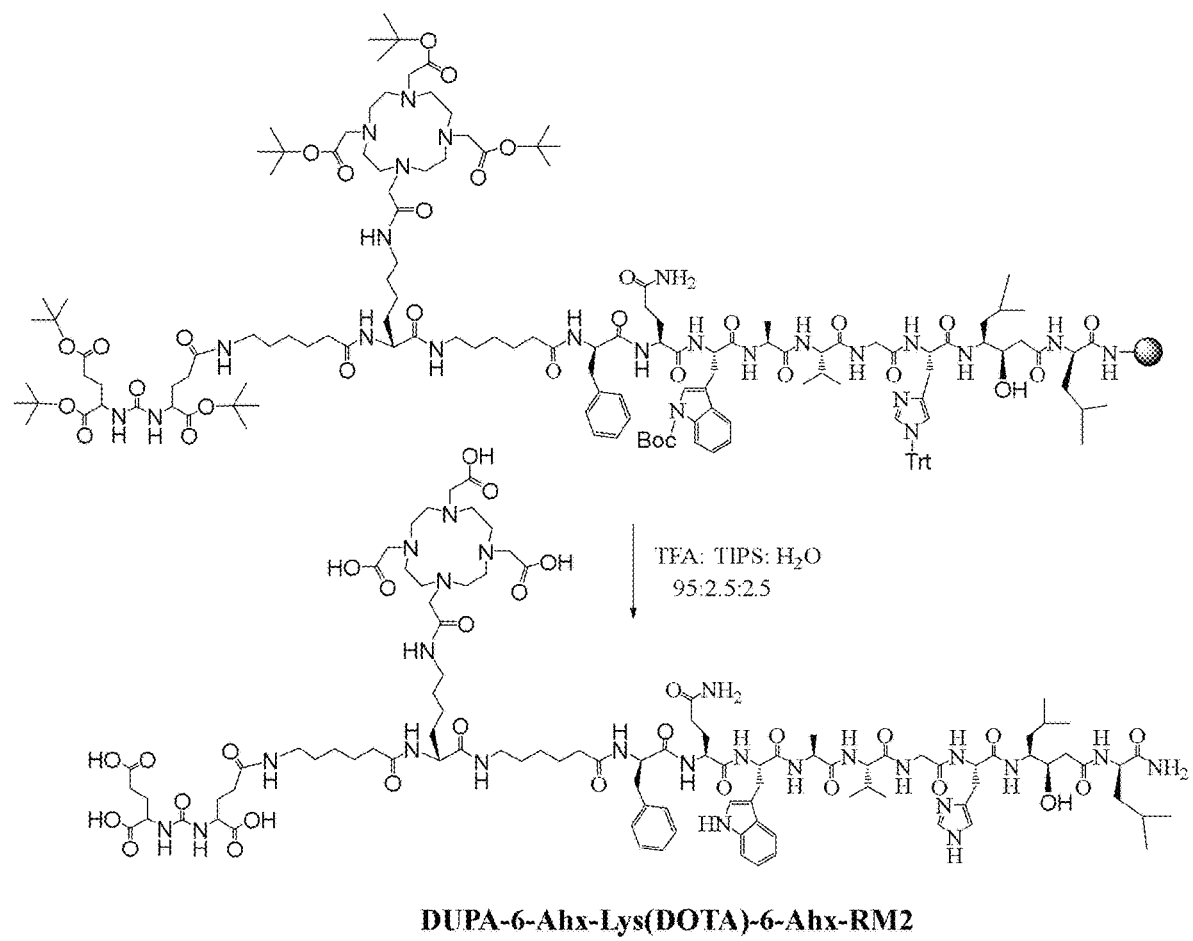

Due to the relatively poor synthetic yields of [DUPA-6-Ahx-Lys(DOTA)-6-Ahx-RM2] under the direct synthetic procedure, the new bivalent agent was also prepared using a (IvDde) protected ε-amine of lysine [Lys-(IvDde)] under a modified synthetic procedure as illustrated in Scheme 2 (FIGS. 6A and 6B). The (IvDde) protecting group was cleaved from the ε-amine of lysine [RM2-6-Ahx-Lys(IvDde)-6-Ahx-NHFmoc] resin using a solution of 2% hydrazine hydrate in dimethyl formamide, agitated for 10 min, and then washed with DMF (4×8.0 mL). Upon swelling, the (IvDde)-deprotected [RM2-6-Ahx-Lys-6-Ahx-NH-Fmoc] resin, was once again suspended in DMF. A solution of DOTA tris(tert-butyl ester) (0.2 mmol), O-Benzotriazole-N,N,N,N-tetramethyl-uronium-hexafluorophosphate (HBTU) (0.2 mmol), Hydroxybenzotriazole (HOBt) (0.2 mmol), and N,N Diisopropylethylamine (DIPEA) (0.4 mmol) in DMF was added to the resin. The resin was bubbled under helium gas for 6 h, after which it was washed with DMF (3×5 mL) and i-PrOH (3×4 mL). The coupling efficiency was assessed by the Kaiser Test, and the [RM2-6-Ahx-Lys(DOTA)-6-Ahx-NH-Fmoc] resin was swelled using a combination of methylene chloride (5 mL) and dimethyl formamide (DMF, 5 mL). A solution of 20% piperidine in DMF (4×4 mL) was added to the [RM2-6-Ahx-Lys(DOTA)-6-Ahx-NH-Fmoc]resin and nitrogen gas was bubbled through it for 5 min. The resin was washed with DMF (4×5 mL) and isopropyl alcohol (iPrOH, 3×3 mL). Formation of the free, N-terminal, primary amine was assessed by the Kaiser Test. Upon swelling the [RM2-6-Ahx-Lys(DOTA)-6-Ahx-NH2] resin once again in DMF, a solution of 2-[3-(1,3-Bis-tert-butoxycarbonylpropyl)-ureido]pentanedioic acid 1-tert-butyl ester (0.2 mmol), O-Benzotriazole-N,N,N',N'-tetramethyl-uronium-hexafluorophosphate (HBTU) (0.2 mmol), Hydroxybenzotriazole (HOBt) (0.2 mmol) and N,N Diisopropylethylamine (DIPEA) (0.4 mmol) in DMF was added to the [RM2-6-Ahx-Lys(DOTA)-6-Ahx-NH2] resin. The resin was bubbled under helium gas for 5 h, after which it was washed with DMF (3×5 mL) and i-PrOH, (3×4 mL). The coupling efficiency was again assessed by the Kaiser Test. A cocktail of water, triisopropylsilane (TIS), and trifluoroacetic acid (TFA) in a ratio of 2.5:2.5:95 was used to cleave the peptide from the resin, followed by peptide precipitation in methyl-t-butyl ether. Solvents were removed in vacuo using a SpeedVac concentrator (Labconco, Kansas City, Mo.) and the crude peptide conjugate was purified by RP-HPLC. The new bivalent peptide/small molecule targeting vector was obtained in 58% yield and was characterized by MALDI-TOF mass spectrometry (Table 1).

Preparation of [DUPA-6-Ahx-Lys($^{nat/*}$M-DOTA)-6-Ahx-RM2]

The protocol for metallation of each conjugate was based upon a previously published procedure [49] with only minor modifications. Briefly, either natural $GaCl_3$ $3H_2O$ or $InCl_3$ $3H_2O$, or $LuCl_3$ $3H_2O$ in 0.05 N HCl (90 nmol) was added to purified [DUPA-6-Ahx-Lys(DOTA)-6-Ahx-RM2] peptide conjugate (90 nmol) dissolved in 250 μl 0.4 M ammonium acetate. Immediately following a 1 hour incubation at 80° C., 50 μL of a 10 mM diethylene-triaminepentaacetic acid (DTPA) was added to the mixture to scavenge remaining unbound metal. The resulting, metallated compounds were purified by RP-HPLC and submitted for MALDI-TOF mass spectrometry characterization prior to in vitro competitive binding assays. Similarly, synthesis of radio conjugates was achieved by the reaction of 50 μg of purified [DUPA-6-Ahx-Lys(DOTA)-6-Ahx-RM2] in 200 μl 0.4 M ammonium acetate with $^{67}$GaCl$_3$ 3H$_2$O (~489 MBq, 1.32× 10$^4$ μCi), $^{111}$InCl$_3$ 3H$_2$O (~436 MBq, 1.18×10$^4$ μCi), or $^{177}$LuCl$_3$ 3H$_2$O (~410 MBq, 1.11×10$^4$ μCi) in 0.05 N HCl for 1 h at 80° C. This was followed by the addition of 50 μL of 10 mM DTPA solution to scavenge the remaining unbound metal. The resulting radio conjugates were purified using RP-HPLC and collected into 10 mg of ascorbic acid dissolved in 100 μL of 1 mg/mL bovine serum albumin (BSA) prior to in vitro stability assays. Acetonitrile was removed under a steady stream of nitrogen, and the radiochemical purity was assessed by RP-HPLC.

In Vitro Assays

In Vitro RP-HPLC Stability Assays

RP-HPLC purified radioconjugates [DUPA-6-Ahx-Lys[$_{67}$Ga-DOTA]-6-Ahx-RM2], [DUPA-6-Ahx-Lys[$^{111}$In-DOTA]-6-Ahx-RM2], and [DUPA-6-Ahx-Lys[$^{77}$Lu-DOTA]-6-Ahx-RM2] were incubated in phosphate-buffered saline and were analyzed by RP-HPLC in order to assess the degree of product degradation due to radiolysis or radionuclide dissociation from the DOTA bifunctional chelating agent. Time-points were assessed at 2, 12, 24, and 48 hours.

In Vitro Competitive Displacement Binding Assays

A competitive displacement binding affinity assay (IC$_{50}$) with purified [DUPA-6-Ahx-Lys-6-Ahx-RM2] and [DUPA-6-Ahx-Lys(DOTA)-6-Ahx-RM2] was performed in GRPR-positive PC-3 cells and PSMA-positive homogenized cell membranes using [$^{125}$I-(Tyr4)-BBN] and [N-acetyl aspartyl $^3$H-glutamate] (NAAG) as the radioligands. For the GRPR-positive assay, 3×10$^4$ PC-3 cells (in D-MEM/F-12 K media containing 0.01 M MEM and 2% BSA, pH=5.5) were incubated with 20,000 counts per minute of [$^{125}$I-(Tyr4)-BBN] and increasing concentrations (1×10$^{-13}$-1×10$^{-5}$ M) of the metallated targeting vector (1 h, 37° C., 5% CO$_2$-enriched atmosphere). After incubation, the reaction medium was aspirated and the cells were rinsed three times with cold media. Cell-associated radioactivity was determined using a Packard Riastar gamma counter. The percent of bound radioligand was plotted against the increasing concentrations of the metallated conjugate to determine the IC$_{50}$ value. IC$_{50}$ values were determined by curve fitting using Prism Software (version 6.0). For the PSMA-positive assay, the binding affinity was measured using the N-acetylated-α-linked acidic dipeptidase (NAALADase) assay with only minor modification [58]. Briefly, [DUPA-6-Ahx-Lys-6-Ahx-RM2] and [DUPA-6-Ahx-Lys(DOTA)-6-Ahx-RM2] (increasing concentrations 1×10$^{-13}$-1×10$^{-5}$ M) in 50 μL of Tris-HCl buffer (50 mM, pH=7.4) were incubated with LNCaP tissue culture homogenized cell membranes for a period of 45 min. Then, [N-acetyl aspartyl $^3$H-glutamate] was added to the reaction mixture and the solution was allowed to incubate for an additional 15 min at 37° C. The enzymatic reaction was stopped by addition of 50 μL of cold sodium phosphate buffer (0.1 M, pH=7.4). [N-acetyl aspartyl $^3$H-glutamate] and [$^3$H-glutamate] were resolved by cation exchange chromatography using AG 50 W-X8 columns (200-400 mesh). Columns were preequilibrated with 0.2 M HCl prior to loading of the reaction mixture. Fractions containing [$^3$H glutamate] were eluted using 6 mL of 2 M HCl. Scintillation cocktail was added to each fraction and the amount of radioactivity in each was determined by liquid scintillation counting. The percent of bound radioligand was plotted against the increasing concentrations of the conjugate to determine the IC$_{50}$ value. IC$_{50}$ values were determined by curve fitting using Prism Software (version 6.0).

Example 2

In this Example, biodistribution studies were conducted.

Biodistribution Studies in Normal Mice

The in vivo behavior of the $^{111}$In-labeled DUPA-6-Ahx-Lys($^{111}$In-DOTA)-X-RM2 of (X=5-Ava, 6-Ahx, 8-Aoc and AMBA) was determined in CF-1 normal mice after intravenous (i.v.) administration of each compound (100 μL, 3-4 MBq, 0.1-0.2 nmol/mouse). The biodistribution (1 hour post-injection (p.i.)) is summarized in Table 2. DUPA-6-Ahx-Lys($^{111}$In-DOTA)-5-Ava-RM2 presented high kidneys (4.92±0.87% ID/g) and pancreas (1.02±37% ID/g) uptake, whereas for DUPA-6-Ahx-Lys($^{111}$In-DOTA)-8-Aoc-RM2 the high uptake was demonstrated in pancreas (5.45±0.47% ID/g) and small intestines (2.20±3.37% ID/g) respectively.

Biodistribution Studies in PC-3 and PC-3PIP Tumor-Bearing Mice

The in vivo behavior of the $^{111}$In-labeled DUPA-6-Ahx-Lys($^{111}$In-DOTA)-8-Aoc-RM2 heterodimer was evaluated in ICR-SCID male mice bearing PSMA positive PC-3PIP and GRPr positive PC-3 tumors (after intravenous (i.v.) administration of each compound (100 μL, 3-4 MBq, 0.1-0.2 nmol/mouse). The results of the respective tumor uptakes for both PC-3 and PC-3PIP tumor models are presented in Table 3, 4 (for the full organ distribution tables), whereas Table 2 summarizes the normal tissue ratios for muscle, kidney, spleen, and liver and Table 3 and 4 summarizes the tumor tissue ratios for muscle, kidney, spleen, and liver. The tumor uptake of DUPA-6-Ahx-Lys($^{111}$In-DOTA)-8-Aoc-RM2 (in tumor-bearing PC-3 mice was 1 hr: 4.74±0.90; 4 hr: 4.70±1.01 and 24 hr: 2.64±1.07% ID/g) whereas accumulation and retention in pancreas was significantly lower (4 hr: 0.58±0.10 and 24 hr: 0.14±0.01% ID/g)).

The uptake/accumulation for DUPA-6-Ahx-Lys($^{111}$In-DOTA)-8-Aoc-RM2 in PC-3PIP tumor-bearing mice was 1 hr: 5.38±1.07; 4 hr: 4.43±0.51 and 24 hr: 1.61±0.50% ID/g, whereas accumulation and retention in pancreas was significantly lower (4 hr: 0.51±0.24 and 24 hr: 0.27±0.08% ID/g). For PC-3 tumor-bearing mice and PC-3PIP tumor-bearing mice, DUPA-6-Ahx-Lys($^{111}$In-DOTA)-8-Aoc-RM2 showed high tumor uptake. The tumor accumulation rate was rather similar in both cases (PC-3 tumor-bearing mice and PC-3PIP tumor-bearing mice), but kidney and pancreas uptake was reduced for PC-3 tumor-bearing mice.

TABLE 2

Biodistribution studies of [DUPA-6-Ahx-[$^{111}$In-DOTA]-X-RM2] in CF-1 normal mice at 1 hr p.i. (% ID/g ± SD, n = 5). X = 5-Ava, 6-Ahx, 8-Aoc, AMBA.

|  | 5-Ava 1 h | 6-Ahx 1 h | 8-Aoc 1 h | AMBA 1 h |
|---|---|---|---|---|
| Heart | 0.11 ± 0.06 | 0.16 ± 0.22 | 0.20 ± 0.14 | 0.12 ± 0.05 |
| Lung | 0.68 ± 0.25 | 0.86 ± 0.70 | 0.37 ± 0.03 | 1.01 ± 1.15 |

TABLE 2-continued

Biodistribution studies of [DUPA-6-Ahx-[$^{111}$In-DOTA]-X-RM2] in
CF-1 normal mice at 1 hr p.i. (% ID/g ± SD, n = 5). X = 5-Ava, 6-Ahx, 8-Aoc, AMBA.

|  | 5-Ava 1 h | 6-Ahx 1 h | 8-Aoc 1 h | AMBA 1 h |
|---|---|---|---|---|
| Liver | 0.15 ± 0.05 | 0.23 ± 0.14 | 0.38 ± 0.04 | 0.28 ± 0.04 |
| Kidneys | 4.92 ± 0.84 | 2.84 ± 0.64 | 1.37 ± 0.31 | 1.37 ± 0.31 |
| Spleen | 0.13 ± 0.05 | 0.12 ± 0.13 | 0.49 ± 0.34 | 0.15 ± 0.04 |
| Stomach | 0.23 ± 0.18 | 0.14 ± 0.11 | 1.73 ± 2.49 | 0.15 ± 0.06 |
| S. Intestine | 0.26 ± 0.09 | 0.22 ± 0.13 | 2.20 ± 3.37 | 0.20 ± 0.04 |
| L. Intestine | 0.12 ± 0.05 | 0.14 ± 0.12 | 0.49 ± 0.25 | 0.09 ± 0.02 |
| Muscle | 0.06 ± 0.04 | 0.07 ± 0.07 | 0.10 ± 0.01 | 0.08 ± 0.02 |
| Bone | 0.09 ± 0.06 | 0.08 ± 0.06 | 0.14 ± 0.04 | 0.06 ± 0.04 |
| Brain | 0.02 ± 0.01 | 0.03 ± 0.04 | 0.02 ± 0.00 | 0.02 ± 0.01 |
| Pancreas | 1.02 ± 0.37 | 0.19 ± 0.19 | 5.45 ± 0.47 | 0.24 ± 0.06 |
| Blood* | 0.24 ± 0.17 | 0.43 ± 0.73 | 0.38 ± 0.14 | 0.26 ± 0.13 |
| Urine* | 91.53 ± 2.22 | 91.00 ± 5.58 | 79.74 ± 6.05 | 88.72 ± 1.96 |

*Data presented as % ID

TABLE 3

Biodistribution studies of [DUPA-6-Ahx-[$^{111}$In-DOTA]-8-Aoc-RM2]
in ICR-SCID PC-3 tumor mice at 1 hr, 4 hr and 24 hr p.i.
(% ID/g ± SD).

|  | 8-Aoc 1 h | 8-Aoc 4 h | 8-Aoc 24 h |
|---|---|---|---|
| Heart | 0.31 ± 0.02 | 0.06 ± 0.03 | 0.03 ± 0.01 |
| Lung | 0.67 ± 0.08 | 0.12 ± 0.03 | 0.04 ± 0.01 |
| Liver | 0.56 ± 0.11 | 0.14 ± 0.04 | 0.10 ± 0.02 |
| Kidneys | 8.90 ± 1.40 | 2.62 ± 0.88 | 0.40 ± 0.20 |
| Spleen | 1.16 ± 0.39 | 0.13 ± 0.04 | 0.10 ± 0.03 |
| Stomach | 0.66 ± 0.12 | 0.19 ± 0.03 | 0.10 ± 0.14 |
| S. Intestine | 0.94 ± 0.16 | 0.27 ± 0.04 | 0.10 ± 0.07 |
| L. Intestine | 0.40 ± 0.11 | 0.64 ± 0.08 | 0.19 ± 0.17 |
| Muscle | 0.13 ± 0.04 | 0.02 ± 0.00 | 0.01 ± 0.00 |
| Bone | 0.17 ± 0.08 | 0.07 ± 0.03 | 0.03 ± 0.01 |
| Brain | 0.04 ± 0.01 | 0.01 ± 0.00 | 0.00 ± 0.00 |
| Pancreas | 9.08 ± 1.88 | 0.58 ± 0.10 | 0.14 ± 0.02 |
| Blood* | 1.19 ± 0.22 | 0.13 ± 0.05 | 0.02 ± 0.00 |
| Urine* | 70.27 ± 11.30 | 93.57 ± 1.19 | 94.09 ± 4.00 |
| Tumor | 4.74 ± 0.90 | 4.70 ± 1.01 | 2.64 ± 1.07 |

*Data presented as % ID

TABLE 4

Biodistribution studies of [DUPA-6-Ahx-[$^{111}$In-DOTA]-8-Aoc-RM2]
in ICR-SCID PC-3PIP tumor mice at 1 hr, 4 hr and 24 hr p.i.
(% ID/g ± SD).

|  | 8-Aoc 1 h | 8-Aoc 4 h | 8-Aoc 24 h |
|---|---|---|---|
| Heart | 0.85 ± 0.33 | 0.16 ± 0.07 | 0.04 ± 0.01 |
| Lung | 1.77 ± 0.52 | 0.35 ± 0.16 | 0.13 ± 0.04 |
| Liver | 1.11 ± 0.33 | 0.39 ± 0.15 | 0.28 ± 0.04 |
| Kidneys | 21.71 ± 7.61 | 3.30 ± 0.69 | 0.93 ± 0.22 |
| Spleen | 2.94 ± 1.14 | 0.41 ± 0.16 | 0.27 ± 0.08 |
| Stomach | 0.87 ± 0.31 | 0.64 ± 0.28 | 0.12 ± 0.06 |
| S. Intestine | 2.33 ± 0.97 | 2.35 ± 3.80 | 0.18 ± 0.09 |
| L. Intestine | 0.77 ± 0.22 | 0.93 ± 0.07 | 0.70 ± 0.40 |
| Muscle | 0.23 ± 0.06 | 0.05 ± 0.02 | 0.02 ± 0.01 |
| Bone | 0.39 ± 0.17 | 0.15 ± 0.11 | 0.10 ± 0.02 |
| Brain | 0.09 ± 0.03 | 0.03 ± 0.01 | 0.01 ± 0.00 |
| Pancreas | 18.02 ± 6.54 | 1.19 ± 0.56 | 0.27 ± 0.08 |
| Blood* | 3.18 ± 0.83 | 0.51 ± 0.24 | 0.07 ± 0.02 |
| Urine* | 60.11 ± 9.83 | 87.72 ± 6.90 | 91.91 ± 3.17 |
| Tumor | 5.38 ± 1.07 | 4.43 ± 0.51 | 1.61 ± 0.50 |

*Data presented as % ID

Example 3

In this Example, in vitro competitive displacement binding assays were conducted.

A competitive displacement binding assay (IC$_{50}$) of [DUPA-6-Ahx-Lys[DOTA]-X-RM2] and [DUPA-6-Ahx-Lys[nat-In/nat-Lu-DOTA]-X-RM2] where X=5-Ava, 6-Ahx, 8-Aoc and AMBA were determined in GRPR-positive PC-3 cells and PSMA-positive homogenized cell membranes using [$^{125}$I-(Tyr4)-BBN] and [N-acetyl aspartyl $^3$H-glutamate] (NAAG) as the radioligands. For the GRPR-positive assay, 3×10$^4$ PC-3 cells (in D-MEM/F-12 K media containing 0.01 M MEM and 2% BSA, pH=5.5) were incubated with 20,000 counts per minute of [$^{125}$I-(Tyr4)-BBN] and increasing concentrations (1×10$^{-13}$-1×10$^{-5}$ M) of the metallated targeting vector (1 h, 37° C., 5% CO$_2$-enriched atmosphere). After incubation, the reaction medium was aspirated and the cells were rinsed three times with cold media. Cell-associated radioactivity was determined using a Packard Riastar gamma counter. The percent of bound radioligand was plotted against the increasing concentrations of the metallated conjugate to determine the IC$_{50}$ value. IC$_{50}$ values were determined by curve fitting using Prism Software (version 6.0). For the PSMA-positive assay, the binding affinity was measured using the N-acetylated-α-linked acidic dipeptidase (NAALADase) assay. Briefly [DUPA-6-Ahx-Lys[DOTA]-X-RM2] and [DUPA-6-Ahx-Lys[nat-In/nat-Lu-DOTA]-X-RM2] (increasing concentrations 1×10$^{-13}$-1×10$^{-5}$ M) in 50 μL of Tris-HCl buffer (50 mM, pH=7.4) were incubated with LNCaP tissue culture homogenized cell membranes for a period of 45 min. Then, [N-acetyl aspartyl $^3$H-glutamate] was added to the reaction mixture and the solution was allowed to incubate for an additional 15 min at 37° C. The enzymatic reaction was stopped by addition of 50 μL of cold sodium phosphate buffer (0.1 M, pH=7.4). [N-acetyl aspartyl $^3$H-glutamate] and [$^3$H-glutamate] were resolved by cation exchange chromatography using AG 50 W-X8 columns (200-400 mesh). Columns were pre-equilibrated with 0.2 M HCl prior to loading of the reaction mixture. Fractions containing [$^3$H-glutamate] were eluted using 6 mL of 2 M HCl. Scintillation cocktail was added to each fraction and the amount of radioactivity in each was determined by liquid scintillation counting. The percent of bound radioligand was plotted against the increasing concentrations of the conjugate to determine the IC$_{50}$ value. IC$_{50}$ values were determined by curve fitting using Prism Software (version 6.0). Results are summarized in Table 5.

TABLE 5

Mass spectrometry, IC$_{50}$, and RP-HPLC data for [DUPA-6-Ahx-[DOTA]-spacer-RM2] and [DUPA-6-Ahx-[nat-In/nat-Lu-DOTA]-spacer-RM2].

| Name of Compound | Molecular Formula | Calculated molecular mass | Observed molecular Mass | IC$_{50}$ PC3 cells | IC$_{50}$ LNCaP cells | HPLC t$_{r(min)}$ |
|---|---|---|---|---|---|---|
| [DUPA-6-Ahx-[DOTA]-5-Ava-RM2] | $C_{99}H_{152}N_{24}O_{29}$ | 2141.44 | 2142.45 | 5.14 ± 1.39 nM | 11.21 ± 2.05 nM | 11.5 |
| [DUPA-6-Ahx-[DOTA]-6-Ahx-RM2] | $C_{100}H_{154}N_{24}O_{29}$ | 2156.44 | 2157.60 | 3.85 ± 1.12 nM | 10.49 ± 2.77 nM | 11.5 |
| [DUPA-6-Ahx-[DOTA]-8-Aoc-RM2] | $C_{102}H_{158}N_{24}O_{29}$ | 2184.45 | 2185.44 | 5.93 ± 1.09 nM | 12.69 ± 2.29 nM | 11.7 |
| [DUPA-6-Ahx-[DOTA]-AMBA-RM2] | $C_{101}H_{148}N_{24}O_{29}$ | 2157.96 | 2159.02 | 5.27 ± 1.31 nM | 11.97 ± 2.73 nM | 11.5 |
| [DUPA-6-Ahx-[$^{nat}$In-DOTA]-5-Ava-RM2] | $C_{99}H_{149}N_{24}O_{29}{}^{nat}In$ | 2253.00 | 2254.04 | 5.74 ± 1.23 nM | 14.37 ± 2.53 nM | 11.8 |
| [DUPA-6-Ahx-[$^{nat}$In-DOTA]-6-Ahx-RM2] | $C_{100}H_{151}N_{24}O_{29}{}^{nat}In$ | 2267.01 | 2268.27 | 4.35 ± 1.47 nM | 13.53 ± 2.96 nM | 11.8 |
| [DUPA-6-Ahx-[$^{nat}$In-DOTA]-8-Aoc-RM2] | $C_{102}H_{155}N_{24}O_{29}{}^{nat}In$ | 2295.04 | 2296.32 | 6.12 ± 1.03 nM | 15.69 ± 2.71 nM | 12.3 |
| [DUPA-6-Ahx-[$^{nat}$In-DOTA-AMBA-RM2] | $C_{101}H_{145}N_{24}O_{29}{}^{nat}In$ | 2272.96 | 2274.23 | 5.73 ± 0.98 nM | 14.87 ± 2.45 nM | 11.8 |
| [DUPA-6-Ahx-[$^{nat}$Lu-DOTA]-5-Ava-RM2] | $C_{99}H_{149}N_{24}O_{29}{}^{nat}Lu$ | 2313.03 | 2314.30 | 5.92 ± 1.11 nM | 14.12 ± 2.17 nM | 11.8 |
| [DUPA-6-Ahx-[$^{nat}$Lu-DOTA]-6-Ahx-RM2] | $C_{100}H_{151}N_{24}O_{29}{}^{nat}Lu$ | 2327.05 | 2328.05 | 4.83 ± 1.19 nM | 13.85 ± 2.53 nM | 11.8 |
| [DUPA-6-Ahx-[$^{nat}$Lu-DOTA]-8-Aoc-RM2] | $C_{102}H_{155}N_{24}O_{29}{}^{nat}Lu$ | 2355.08 | 2356.08 | 6.49 ± 1.26 nM | 15.95 ± 2.79 nM | 12.3 |
| [DUPA-6-Ahx-[$^{nat}$Lu-DOTA]-AMBA-RM2 | $C_{101}H_{145}N_{24}O_{29}{}^{nat}Lu$ | 2333.3 | 2334.38 | 5.51 ± 1.43 nM | 15.09 ± 2.64 nM | 11.8 |

Results

Figure 2:
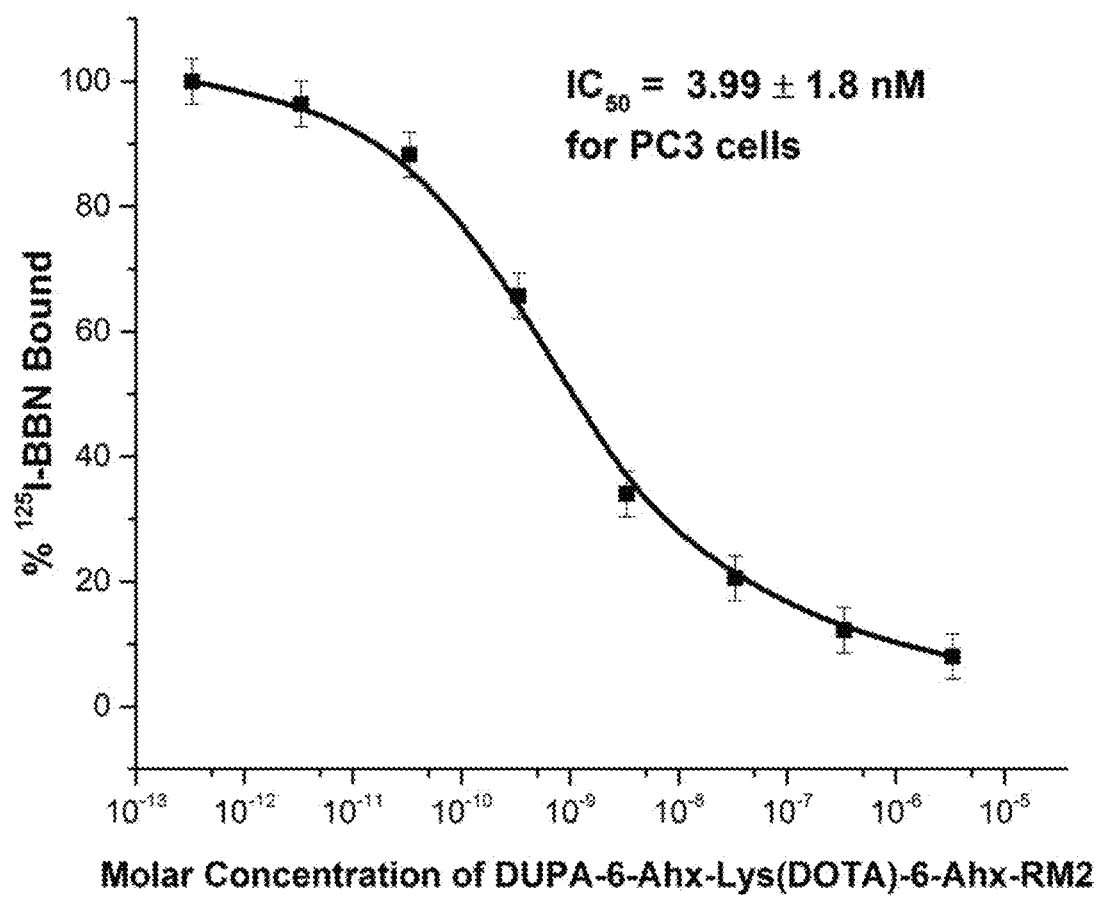
FIG. 2 depicts the inhibitory concentration half maximum ($IC_{50}$) of [DUPA-6-Ahx-Lys(M-DOTA)-6-Ahx-RM2] (IC50=3.99±1.80 nM in PC-3 cells).
Figure 3:
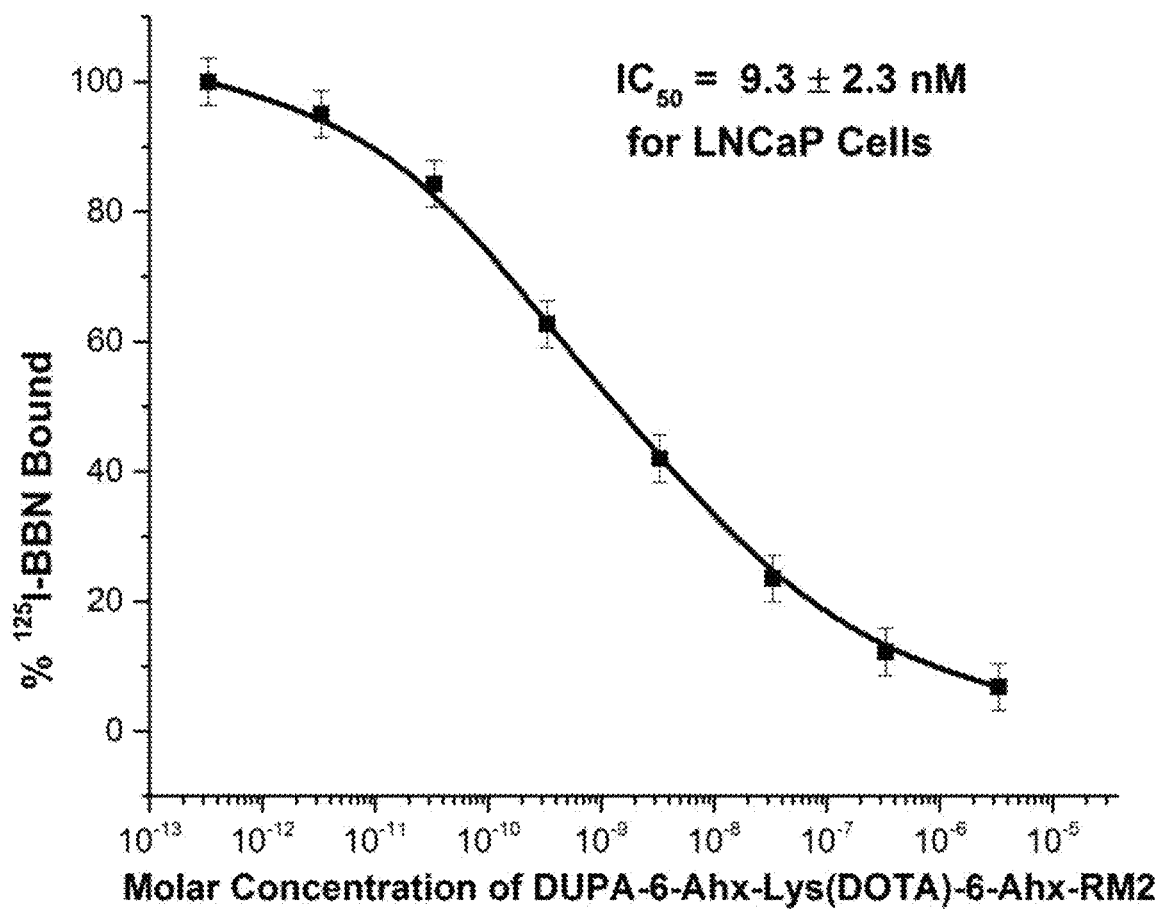
FIG. 3 depicts the inhibitory concentration half maximum ($IC_{50}$) of [DUPA-6-Ahx-Lys(M-DOTA)-6-Ahx-RM2] (IC50=9.3±2.32 nM in LNCaP cells).
Figure 4:
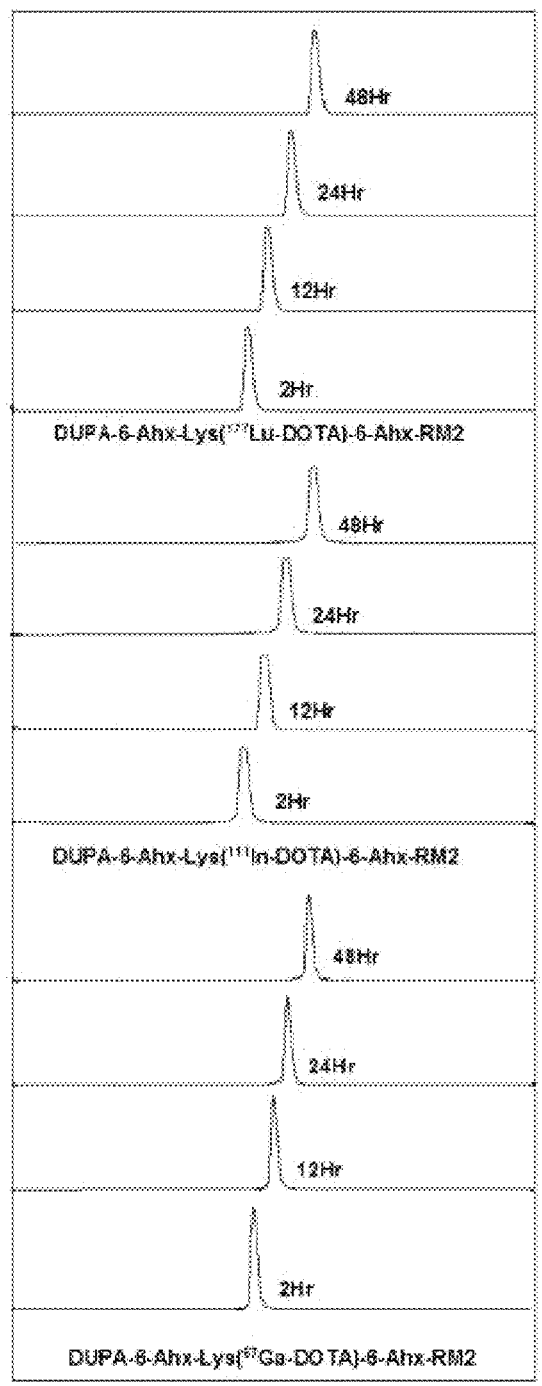
FIG. 4 depicts HPLC chromatographic profiles in phosphate buffered saline for [DUPA-6-Ahx-Lys($^{177}$Lu-DOTA)-6-Ahx-RM2], [DUPA-6-Ahx-Lys($^{67}$Ga-DOTA)-6-Ahx-RM2], and [DUPA-6-Ahx-Lys($^{111}$In-DOTA)-6-Ahx-RM2].
Figure 5A:
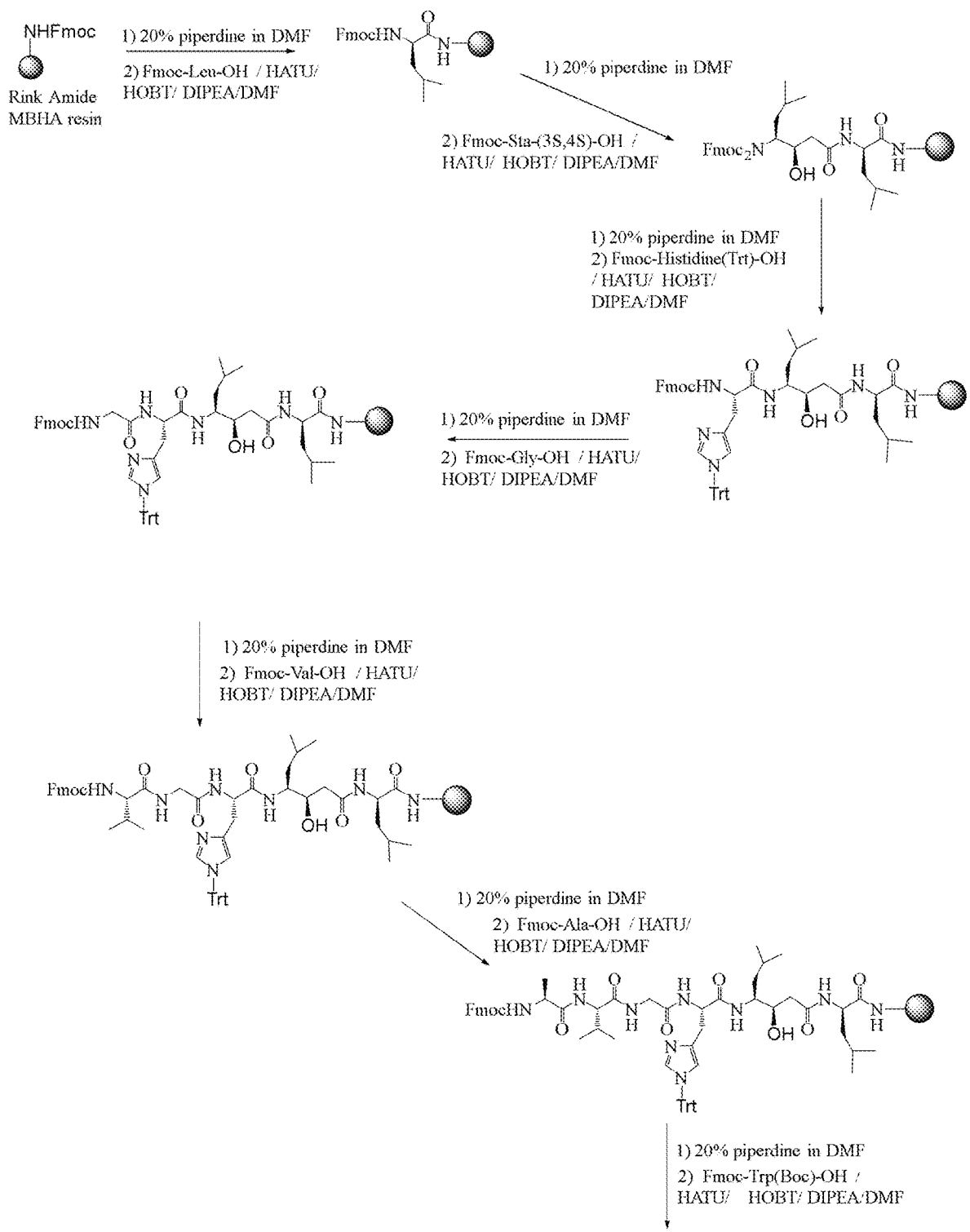
FIGS. 5A-5D depict synthetic scheme 1.
Figure 5B:
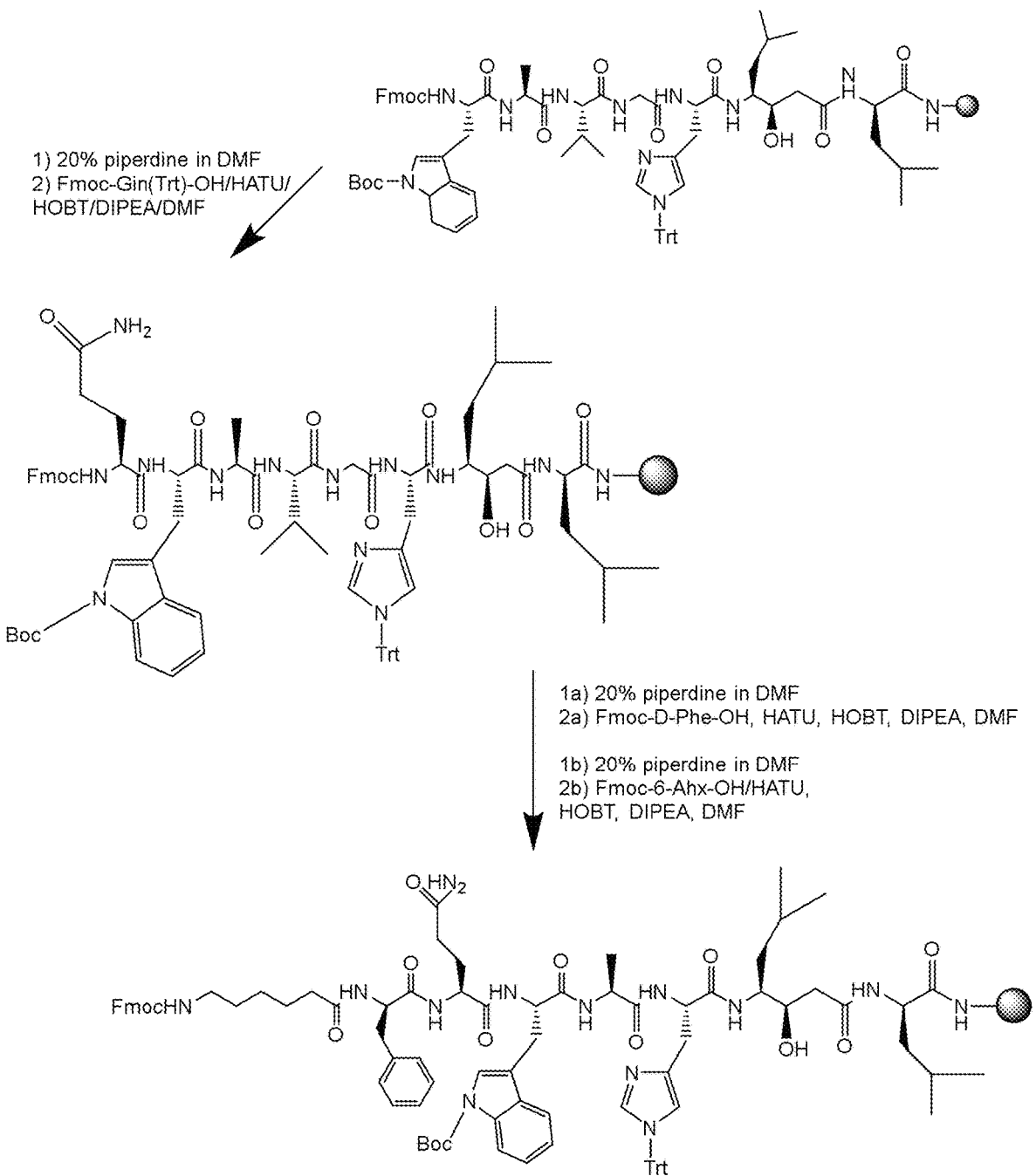
Figure 5C:
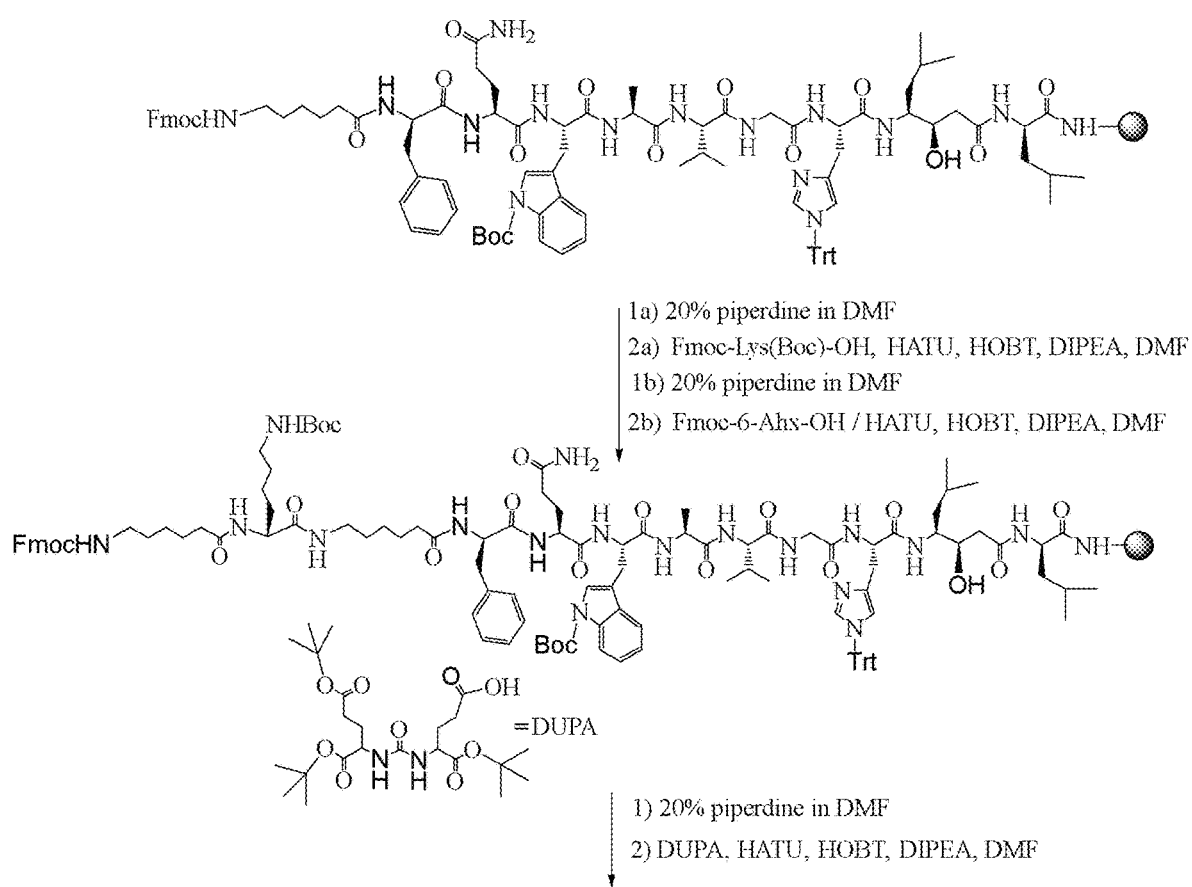
Figure 5D:
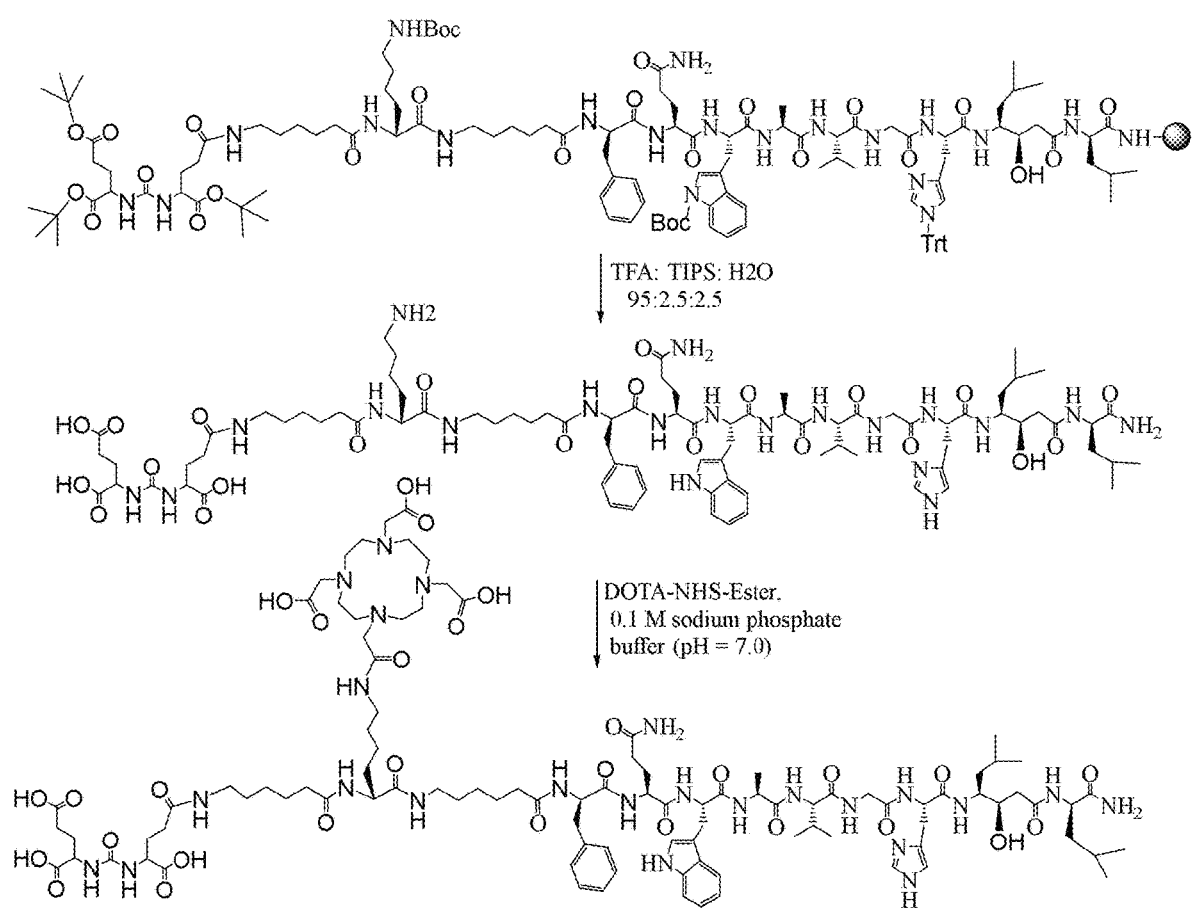

The novel, dual-biomarker, targeting ligands described herein have high affinity and specificity for PSMA/GRPR. [DUPA-6-Ahx-Lys(DOTA)-6-Ahx-RM2] and its metallated conjugates are the first of their kind for this new family of dual-biomarker targeting agents. In the Examples, 2-[3-(1, 3-Bis-tert-butoxycarbonylpropyl)-ureido]pentanedioic acid 1-tert-butyl ester (DUPA precursor) was prepared, purified by flash chromatography, and characterized by ESI-MS and $^1$H/$^{13}$C NMR spectroscopy. Deprotection by hydrogenation afforded 2-[3-(1,3-Bis-tert-butoxycarbonylpropyl)-ureido]pentanedioic acid 1-tert-butyl ester. The PSMA/GRPR dual targeting ligand precursor [DUPA-6-Ahx-Lys-6-Ahx-RM2] conjugate, was first originally prepared by solid-phase peptide synthesis (SPPS) with 2-[3-(1,3-Bis-tert-butoxycarbonylpropyl)-ureido]pentanedioic acid 1-tert-butyl ester being the final addition to the sequence. In the final procedure for preparation of the bivalent agent, DOTA-tris(tBu) NHS active ester was conjugated to [DUPA-6-Ahx-Lys-6-Ahx-RM2]. However, the DOTA-conjugated product [DUPA-6-Ahx-Lys(DOTA)-6-Ahx-RM2] was obtained in poor yield (35%, FIGS. 5A-5D). A modified new synthesis of the PSMA/GRPR targeting precursor [DUPA-6-Ahx-Lys(DOTA)-6-Ahx-RM2] improved the yield significantly (58%, FIGS. 6A and 6B). The Lys(Boc) protection group and Rink Amide-MBHA resin are acid sensitive. Therefore, a Lys(IvDde) precursor for [RM2-6-Ahx-Lys(IvDde)-6-Ahx-NH-Fmoc] preparation was used in this synthetic protocol. The (IvDde) protecting group was cleaved from ε-amine of lysine [RM2-6-Ahx-Lys(IvDde)-6-Ahx-NH-Fmoc]resin by a solution of 2% hydrazine hydrate in dimethyl formamide, agitated for 10 min, followed by washing with DMF. Stepwise addition of a solution of DOTA-tris (tert-butyl ester) was performed manually, followed by deprotection. The new, bivalent PSMA/GRPR targeting vector was purified by RP-HPLC and characterized by MALDI-TOF and the new DOTA conjugate was metallated with $^{nat}$GaCl$_3$, $^{nat}$LuCl$_3$, and $^{nat}$InCl$_3$ to produce [DUPA-6-Ahx-Lys($^{nat}$M-DOTA)-6-Ahx-RM2]. Radiolabeling of the conjugate with $^{177}$Lu, $^{67}$Ga, and $^{111}$In produced DUPA-6-Ahx-Lys($^{177}$Lu-DOTA)-6-Ahx-RM2], [DUPA-6-Ahx-Lys ($^{67}$Ga-DOTA)-6-Ahx-RM2], and [DUPA-6-Ahx-Lys($^{111}$In-DOTA)-6-Ahx-RM2] in high radiochemical yield and purity. All metallated [DUPA-6-Ahx-Lys($^{nat*}$M-DOTA)-6-Ahx-RM2] conjugates (FIG. 1) were purified by RP-HPLC. Natural and radiometallated conjugates were produced in high yield (>95%) as verified by quality control chromatograms and under-the-curve RP-HPLC analyses. While the unmetallated conjugate eluted with a retention time of 9.8 min, all metallated conjugates exhibited slightly shorter retention times, ranging from 9.2 to 9.3 min (Table 1, FIG. 4). This was not unexpected and reflected structural similarity of the compounds as well as the minor effect of coordinate bonding of the different metals within the DOTA complexing agent and a resultant change in charge density, along with slight atomic mass variation. Mass spectrometry analyses were consistent with the calculated molecular weights for each analog (Table 1), further supporting the identification and characterization of the conjugates. Stability assays for three radioconjugates of [DUPA-6-Ahx-Lys(DOTA)-6-Ahx-RM2] are shown in FIG. 4. For the three radioconjugates, HPLC chromatographic traces indicated very good stability. There were no overt changes in the traces of either of the three tracers for the 0-24 h time-points. Very minor variation was observed at the 48 hour time-points, likely representing mild, radiolytic degradation of the otherwise pure, radiolabeled conjugates. Results suggest that three compounds possess adequate stability for use as diagnostic imaging agents or therapy. Competitive displacement receptor binding assays in human prostate PC-3 cells using $^{125}$I-[Tyr4]BBN as the radioligand showed high binding affinity of the [DUPA-6-Ahx-Lys(DOTA)-6-Ahx-RM2] conjugate for the GRPR ($IC_{50}$=3.99±1.80 nM) (FIG. 2). For the PSMA, the binding affinity was measured using the N-acetylated-α-linked acidic dipeptidase (NAALADase) assay in human prostate LNCaP cells with [N-acetyl aspartyl $^3$H-glutamate] being the radioligand of choice. [DUPA-6-Ahx-Lys(DOTA)-6-Ahx-RM2] conjugate exhibited high binding for the PSMA ($IC_{50}$=9.30±2.32 nM) (FIG. 3).

Example 4

In this Example, in vitro competitive displacement binding assays were conducted.

A competitive displacement binding assay ($IC_{50}$) of [DUPA-6-Ahx-Lys[DOTA]-spacer-RM2] and [DUPA-6-Ahx-Lys[nat-In/nat-Lu-DOTA]-spacer-RM2] where spacer=5-Ava, 6-Ahx, 8-Aoc and AMBA were determined in GRPR-positive PC-3 cells and PSMA-positive homogenized cell membranes using [$^{125}$I-(Tyr4)-BBN] and [N-acetyl aspartyl $^3$H-glutamate](NAAG) as the radioligands. For the GRPR-positive assay, 3×10$^4$ PC-3 cells (in D-MEM/F-12 K media containing 0.01 M MEM and 2% BSA, pH=5.5) were incubated with 20,000 counts per minute of [$^{125}$I-(Tyr4)-BBN] and increasing concentrations (1×10$^{-13}$-1×10$^{-5}$ M) of the metallated targeting vector (1 h, 37° C., 5% CO$_2$-enriched atmosphere). After incubation, the reaction medium was aspirated and the cells were rinsed three times with cold media. Cell-associated radioactivity was determined using a Packard Riastar gamma counter. The percent of bound radioligand was plotted against the increasing concentrations of the metallated conjugate to determine the $IC_{50}$ value. $IC_{50}$ values were determined by curve fitting using Prism Software (version 6.0). For the PSMA-positive assay, the binding affinity was measured using the N-acetylated-α-linked acidic dipeptidase (NAALADase) assay. Briefly [DUPA-6-Ahx-Lys[DOTA]-spacer-RM2] and [DUPA-6-Ahx-Lys[nat-In/nat-Lu-DOTA]-spacer-RM2] (increasing concentrations 1×10$^{-113}$-1×10$^{-5}$ M) in 50 µL of Tris-HCl buffer (50 mM, pH=7.4) were incubated with LNCaP tissue culture homogenized cell membranes for a period of 45 min. Then, [N-acetyl aspartyl $^3$H-glutamate] was added to the reaction mixture and the solution was allowed to incubate for an additional 15 min at 37° C. The enzymatic reaction was stopped by addition of 50 µL of cold sodium phosphate buffer (0.1 M, pH=7.4). [N-acetyl aspartyl $^3$H-glutamate] and [$^3$H-glutamate] were resolved by cation exchange chromatography using AG 50 W-X8 columns (200-400 mesh). Columns were pre-equilibrated with 0.2 M HCl prior to loading of the reaction mixture. Fractions containing [$^3$H-glutamate] were eluted using 6 mL of 2 M HCl. Scintillation cocktail was added to each fraction and the amount of radioactivity in each was determined by liquid scintillation counting. The percent of bound radioligand was plotted against the increasing concentrations of the conjugate to determine the $IC_{50}$ value. $IC_{50}$ values were determined by curve fitting using Prism Software (version 6.0).

In this study, a novel, dual-biomarker, targeting ligand having high affinity and specificity for PSMA/GRPr receptors that are expressed on most prostate cancers was prepared. [DUPA-6-Ahx-Lys(DOTA)-X-RM2] was synthesized and the new conjugate was metallated macroscopically with GaCl$_3$, InCl$_3$, and LuCl$_3$ to form [DUPA-6-Ahx-Lys(M-DOTA)-X-RM2](where M=Ga, In, or Lu). These new agents, when radiolabeled with M=In-111 or Lu-177 hold theranostic potential for patients presenting with prostate cancer disease.

X=5-Ava, 6-Ahx, 8Aoc, AMBA

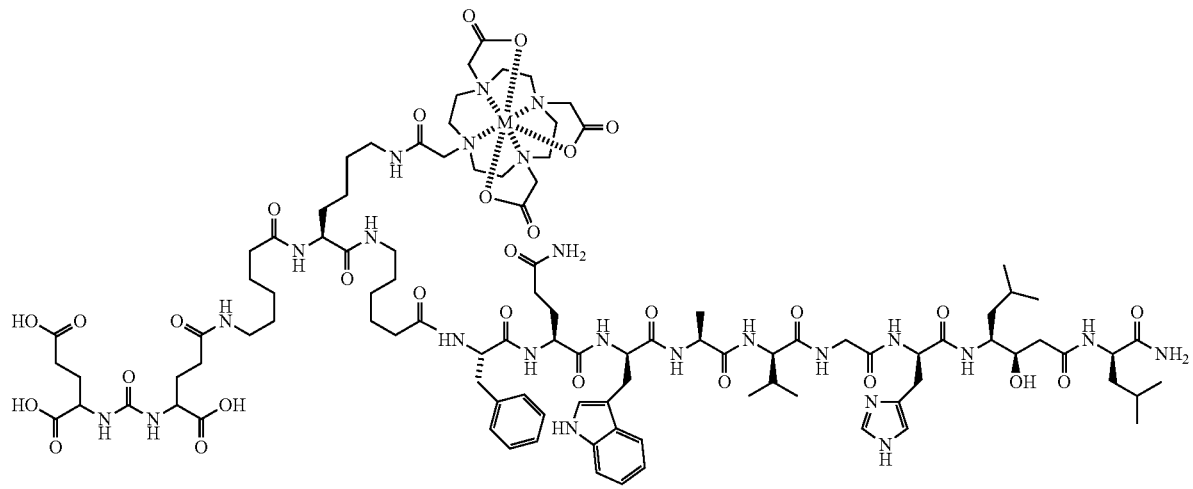

DUPA-6-Ahx-Lys(M-DOTA)-6-Ahx-RM2

-continued

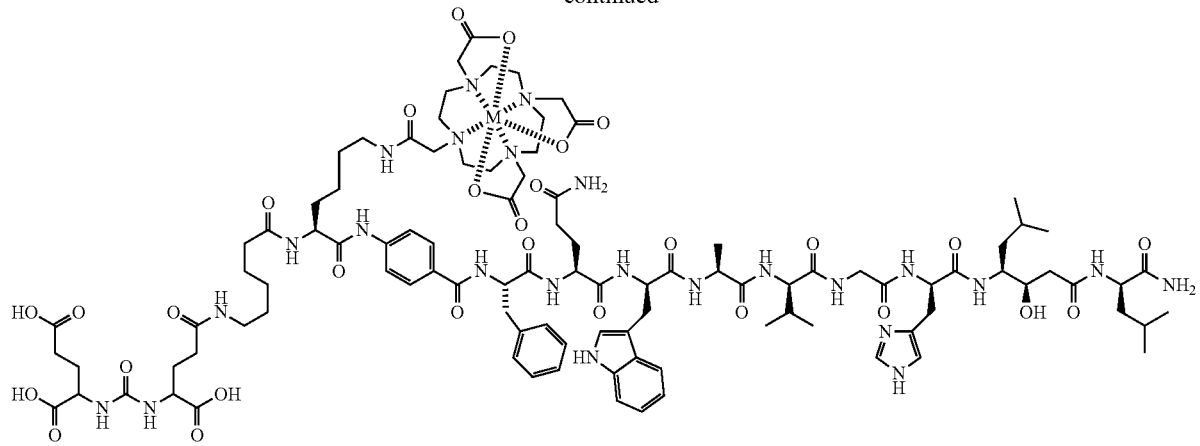

DUPA-6-Ahx-Lys(M-DOTA)-AMBA-RM2

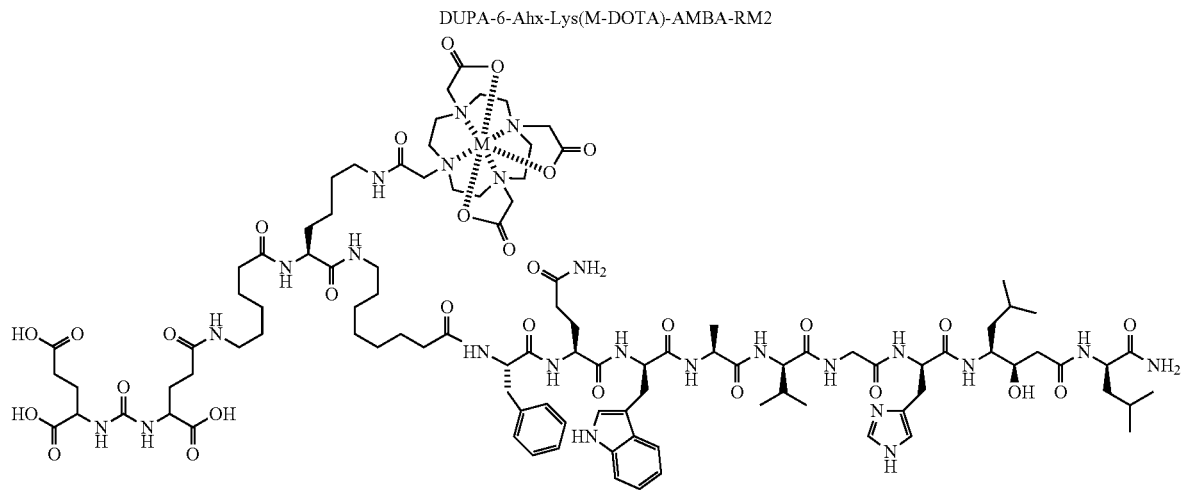

DUPA-6-Ahx-Lys(M-DOTA)-8-Aoc-RM2

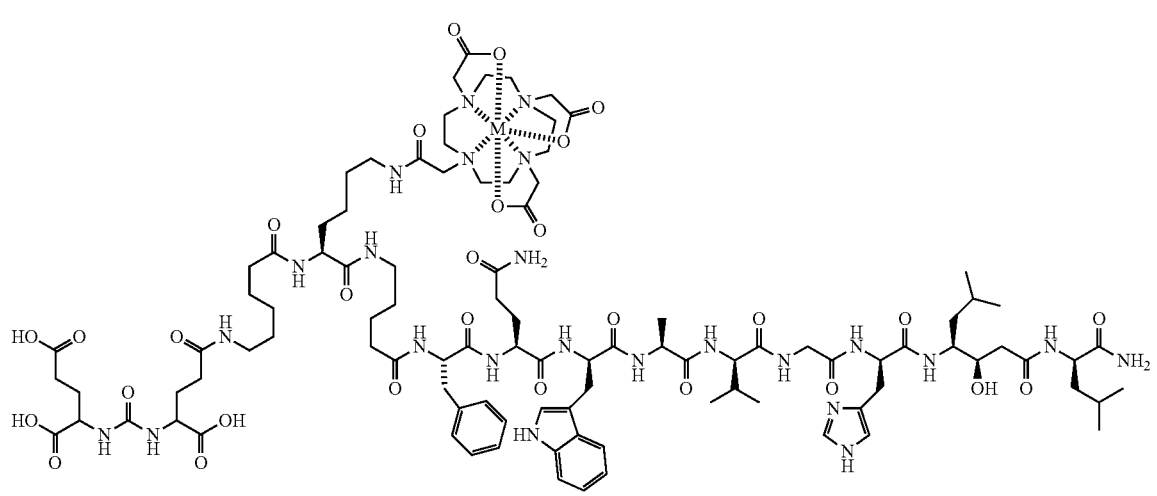

DUPA-6-Ahx-Lys(M-DOTA)-5-Ava-RM2

The results presented herein demonstrate that PSMA and the GRPR can serve as useful biomarkers for bivalent molecular targeting agents for diagnosis of disease via positron-emission tomography (PET) or singlephoton emission computed tomography (SPECT) and radiotherapy. Disclosed herein is the preparation of novel, dual-biomarker, targeting ligands having high affinity and specificity for PSMA/GRPR biomarkers. [DUPA-6-Ahx-Lys(DOTA)-6-Ahx-RM2] was synthesized by manual solid-phase peptide synthesis. The new conjugates were metallated with $^{nat/67}GaCl_3$, $^{nat/111}InCl_3$, and $^{nat/177}LuCl_3$ to form [DUPA-6-Ahx-Lys($^{nat/*}$M-DOTA)-6-Ahx-RM2] (FIG. 1)

These new complexes were characterized by MALDI-TOF mass spectrometry. Detailed in vitro and stability investigations of this new bivalent PSMA/GRPR targeting agent are described herein.

wherein M is selected from Gallium (Ga), Indium (In), Lutetium (Lu), Yttrium (Y), Samarium (Sm), Promethium (Pm), $^{67}$Ga, $^{68}$Ga, $^{111}$In, $^{177}$Lu, $^{90}$Y, $^{86}$Y, $^{153}$Sm, and $^{149}$Pm.

What is claimed is:

1. A bivalent binding agent of formula (I)

[DUPA-6-Ahx-Lys(DOTA)-X-RM2]    (I)

wherein X is selected from the group consisting of 5-aminovaleric acid (5-Ava), 6-amino hexanoic acid (6-Ahx), 8-aminooctanoic acid) (8Aoc), and paraamino benzoic acid (AMBA).

2. A bivalent binding agent of formula (II)

[DUPA-6-Ahx-Lys(M-DOTA)-X-RM2]    (II)

wherein X is selected from 5-aminovaleric acid (5-Ava), 6-amino hexanoic acid (6-Ahx), 8-aminooctanoic acid) (8Aoc), and paraamino benzoic acid (AMBA); and 3. A method of imaging a tissue in a subject in need thereof having or suspected of having prostate cancer, the method comprising:

administering to the subject having or suspected of having prostate cancer a bivalent binding agent of formula (II)

[DUPA-6-Ahx-Lys(M-DOTA)-X-RM2]    (II)

wherein X is selected from 5-aminovaleric acid (5-Ava), 6-amino hexanoic acid (6-Ahx), 8-aminooctanoic acid) (8Aoc), and paraamino benzoic acid (AMBA); and wherein M is selected from $^{67}$Ga, $^{68}$Ga, $^{111}$In, $^{86}$Y, and $^{177}$Lu; and applying an imaging technique to detect emitted gamma rays.

4. The method of claim 3, wherein the imaging technique is selected from the group consisting of positron-emission tomography (PET) and single photon emission computed tomography (SPECT).

5. A method of diagnosing prostate cancer in a subject having or suspected of having prostate cancer, the method comprising:
    administering to the subject a bivalent binding agent of formula (II)

[DUPA-6-Ahx-Lys(M-DOTA)-X-RM2]     (II)

wherein X is selected from 5-aminovaleric acid (5-Ava), 6-amino hexanoic acid (6-Ahx), 8-aminooctanoic acid) (8Aoc), and paraamino benzoic acid (AMBA); and wherein M is selected from $^{67}$Ga, $^{68}$Ga, $^{111}$In, $^{86}$Y, and $^{177}$Lu; applying an imaging technique to detect emitted gamma rays; and diagnosing the subject as having prostate cancer based on uptake of the bivalent binding agent as detected in the imaging of the subject.

6. The method of claim 5, wherein the imaging technique is selected from the group consisting of positron-emission tomography (PET) and single photon emission computed tomography (SPECT).

7. A method of treating prostate cancer in a subject having or suspected of having prostate cancer, the method comprising:
    administering to the subject a bivalent binding agent of formula (II)

[DUPA-6-Ahx-Lys(M-DOTA)-X-RM2]     (II)

wherein X is selected from 5-aminovaleric acid (5-Ava), 6-amino hexanoic acid (6-Ahx), 8-aminooctanoic acid) (8Aoc), and paraamino benzoic acid (AMBA); and wherein M is selected from $^{177}$Lu, $^{90}$Y, $^{153}$Sm, and $^{149}$Pm.

8. The method of claim 7, wherein the subject is administered about 100 μg/70 kg of the bivalent binding agent of formula (II).

9. The method of claim 7, wherein the subject is administered less than 100 μg/70 kg of the bivalent binding agent of formula (II).

* * * * *